(12) United States Patent
Plyte et al.

(10) Patent No.: US 11,993,654 B2
(45) Date of Patent: May 28, 2024

(54) PD-1 BINDING DOMAINS

(71) Applicants: MERUS N.V., Utrecht (NL); INCYTE CORPORATION, Wilmington, DE (US)

(72) Inventors: Simon Edward Plyte, Utrecht (NL); Patrick Mayes, Wilmington, DE (US); Horacio G. Nastri, Wilmington, DE (US); Shaun M. Stewart, Wilmington, DE (US); Rebecca A. Buonpane, Wilmington, DE (US)

(73) Assignees: MERUS N.V., Utrecht (NL); INCYTE CORPORATION, Wilmington, DE (US)

( * ) Notice: Subject to any disclaimer, the term of this patent is extended or adjusted under 35 U.S.C. 154(b) by 0 days.

(21) Appl. No.: 17/710,243

(22) Filed: Mar. 31, 2022

(65) Prior Publication Data
US 2023/0036061 A1 Feb. 2, 2023

(30) Foreign Application Priority Data
Mar. 31, 2021 (NL) .................................. 2027892

(51) Int. Cl.
*C07K 16/28* (2006.01)

(52) U.S. Cl.
CPC ...... *C07K 16/2818* (2013.01); *C07K 2317/31* (2013.01); *C07K 2317/35* (2013.01); *C07K 2317/522* (2013.01); *C07K 2317/524* (2013.01); *C07K 2317/526* (2013.01); *C07K 2317/53* (2013.01); *C07K 2317/565* (2013.01); *C07K 2317/76* (2013.01); *C07K 2317/92* (2013.01)

(58) Field of Classification Search
CPC ................................................ C07K 16/2818
See application file for complete search history.

(56) References Cited

U.S. PATENT DOCUMENTS

| | | | |
|---|---|---|---|
| 9,701,749 B2 | 7/2017 | Shibayama et al. | |
| 2018/0127501 A1* | 5/2018 | Bernett | C07K 16/2818 |
| 2019/0322749 A1* | 10/2019 | Edwards | A61P 35/00 |
| 2020/0325227 A1* | 10/2020 | Geuijen | C07K 16/2827 |

FOREIGN PATENT DOCUMENTS

| | | | |
|---|---|---|---|
| EP | 3 486 257 | 5/2019 | |
| EP | 3 495 390 | 6/2019 | |
| WO | 2006/121168 | 11/2006 | |
| WO | WO-2006121168 A1 * | 11/2006 | A61K 39/00 |
| WO | 2010/029434 | 3/2010 | |
| WO | 2010/029435 | 3/2010 | |
| WO | 2012/145493 | 10/2012 | |
| WO | 2016/011069 | 1/2016 | |
| WO | 2017/049143 | 3/2017 | |
| WO | 2017/058115 | 4/2017 | |
| WO | 2018/053401 | 3/2018 | |
| WO | 2018/053405 | 3/2018 | |
| WO | 2018/162944 | 9/2018 | |
| WO | 2019/009728 | 1/2019 | |
| WO | 2020/015722 | 1/2020 | |
| WO | 2021/243028 | 12/2021 | |

OTHER PUBLICATIONS

U.S. Appl. No. 17/708,901 filed Mar. 2021, Merus N.V.*
Mariuzza (Annu. Rev. Biophys. Biophys. Chem., 16: 139-159, 1987) (Year: 1987).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Ching, KH, et al., Common light chain chickens produce human antibodies of high affinity and broad epitope coverage for the engineering of bispecifics, https://doi.org/10.1080/19420862.2020. 1862451 (Year: 2020).*
Fessas,P, et al., A molecular and preclinical comparison of the PD-1-targeted T-cell checkpoint inhibitors nivolumab and pembrolizumab. Semin Oncol. Apr. 2017;44(2):136-140. doi: 10.1053/ j.seminoncol.2017.06.002. Epub Jul. 4, 2017. PMID: 28923212; PMCID: PMC5612055. (Year: 2017).*
Nivolumab, Kegg, retrieved from: https://www.genome.jp/dbget-bin/www_bget?dr:D10316#:~:text=143597.3811%20Sequence,% 28Heavy%20chain%29 (Year: 2023).*
Choi et al., "Predicting the Functional Effect of Amino Acid Substitutions and Indels", Functional Impacts of Amino Acid Variants, 2012, vol. 7, Issue 10, e46688, pp. 1-13.
Araya et al., "Deep mutational scanning: assessing protein function on a massive scale", Trends Biotechnol., 2011, vol. 29, No. 9, pp. 435-442.
Al-Lazikani et al., "Standard Conformations for the Canonical Structures of Immunoglobulins", J. Mol. Biol., 1997, vol. 273, pp. 927-948.

(Continued)

*Primary Examiner* — Gregory S Emch
*Assistant Examiner* — Ashley H. Gao
(74) *Attorney, Agent, or Firm* — Wenderoth, Lind & Ponack, L.L.P.

(57) ABSTRACT

The present disclosure relates to novel PD-1 binding domains that have a higher binding affinity for human PD-1 than a reference PD-1 binding domain. The PD-1 binding domains of the present disclosure further provide a comparable, or equal or higher, potency in blocking ligand binding to human PD-1 than a reference PD-1 antibody. The present disclosure further relates to binding moieties comprising such PD-1 binding domains. Also provided is a method for treating a disease, in particular a disease associated with a suppressed immune system, such as cancer, with a PD-1 binding domain or binding moiety of the present disclosure. The present disclosure further relates to nucleic acids encoding the heavy chain variable region of the PD-1 binding domains, and a vector and cell comprising such nucleic acid.

20 Claims, 3 Drawing Sheets

Specification includes a Sequence Listing.

(56) References Cited

OTHER PUBLICATIONS

Abhinandan et al., "Analysis and improvements to Kabat and structurally correct numbering of antibody variable domains", Molecular Immunology, 2008, vol. 45, pp. 3832-3839.

Tabasinezhad et al., "Trends in therapeutic antibody affinity maturation: From in-vitro towards next-generation sequencing approaches", Immunology Letters, 2019, vol. 212, pp. 106-113.

Sruthi et al., "Deep2Full: Evaluating strategies for selecting the minimal mutational experiments for optimal computational predictions of deep mutational scan outcomes", PLOS One, 2020, vol. 15, No. 1: e0227621, pp. 1-18.

Munro et al., "DeMaSk: a deep mutational scanning substitution matrix and its use for variant impact prediction", Bioinformatics, 2020, vol. 36, Nos. 22-23, pp. 5322-5329.

MacCallum et al., "Antibody-antigen Interactions: Contact Analysis and Binding Site Topography", J. Mol. Biol., 1996, vol. 262, pp. 732-745.

Lefranc et al., "IMGT unique numbering for immunoglobulin and T cell receptor variable domains and Ig superfamily V-like domains", Developmental and Comparative Immunology, 2003, vol. 27, pp. 55-77.

Kabat et al., "Unusual Distributions of Amino Acids in Complementarity-determining (Hypervariable) Segments of Heavy and Light Chains of Immunoglobulins and Their Possible Roles in Specificity of Antibody-combining Sites", The Journal of Biological Chemistry, 1977, vol. 252, No. 19, pp. 6609-6616.

Honegger et al., "Yet Another Numbering Scheme for Immunoglobulin Variable Domains: An Automatic Modeling and Analysis Tool", J. Mol. Biol., 2001, vol. 309, pp. 657-670.

Haenel et al., "Characterization of high-affinity antibodies by electrochemiluminescence-based equilibrium titration", Analytical Biochemistry, 2005, vol. 339, No. 1, pp. 182-184.

Veronique Giudicelli et al., "IMGT, the international ImMunoGeneTics database", Nucleic Acids Research, 1997, vol. 25, No. 1, pp. 206-211.

Friguet et al., "Measurements of the True Affinity Constant in Solution of Antigen-Antibody Complexes by Enzyme-Linked Immunosorbent Assay", Journal of Immunological Methods, 1985, vol. 77, pp. 305-319.

Cunningham et al., "High-Resolution Epitope Mapping of hGH-Receptor Interactions by Alanine-Scanning Mutagenesis", Science, 1989, vol. 244, No. 4908, pp. 1081-1085.

Chothia et al., "Conformations of immunoglobulin hypervariable regions", Nature, 1989, vol. 342, No. 21, pp. 877-883.

Chothia et al., "Canonical Structures for the Hypervariable Regions of Immunoglobulins", J. Mol. Biol., 1987, vol. 196, pp. 901-917.

Changyu Wang et al., "In Vitro Characterization of the Anti-PD-1 Antibody Nivolumab, BMS-936558, and In Vivo Toxicology in Non-Human Primates", Cancer: Immunology Research, 2014, vol. 2, No. 9, pp. 846-856.

\* cited by examiner

Figure 2

| IgG comprising PD-1 binding domain with SEQ ID NO: | $K_{on}$ | $K_{off}$ | $K_D$ |
|---|---|---|---|
| SEQ ID NO: 1 | 6.67E+05 | 2.55E-04 | 3.82E-10 |
| SEQ ID NO: 6 | 2.48E+05 | 1.93E-04 | 7.81E-10 |
| SEQ ID NO: 5 | 3.95E+05 | 2.18E-04 | 5.51E-10 |
| SEQ ID NO: 11 / SEQ ID NO: 14 x SEQ ID NO: 15 / SEQ ID NO: 16 | 2.13E+05 | 1.59E-03 | 7.49E-09 |
| SEQ ID NO: 11 / SEQ ID NO: 14 | 2.16E+05 | 1.68E-03 | 7.77E-09 |
| SEQ ID NO: 11 / SEQ ID NO: 14 | 2.08E+05 | 1.62E-03 | 7.78E-09 |
| SEQ ID NO: 11 / SEQ ID NO: 14 | 2.07E+05 | 1.64E-03 | 7.92E-09 |
| SEQ ID NO: 11 / SEQ ID NO: 14 | 1.71E+05 | 1.63E-03 | 9.54E-09 |

Figure 3

| Antigen | huPD-1 | | | cyPD-1 | | | Simultaneous binding |
|---|---|---|---|---|---|---|---|
| Antibody | $K_{on}$ (1/Ms) | $K_{off}$ (1/s) | $K_D$ (nM) | $K_{on}$ (1/Ms) | $K_{off}$ (1/s) | $K_D$ (nM) | |
| SEQ ID NO: 7 x Antigen A | 3.08E+05 | 1.20E-04 | 0.39 | 2.94E+05 | 1.29E-04 | 0.44 | Yes |
| SEQ ID NO: 8 x Antigen A | 3.23E+05 | 1.05E-04 | 0.32 | 3.35E+05 | 9.76E-04 | 2.91 | Yes |
| Reference antibody Antigen A | - | - | - | - | - | - | - |
| SEQ ID NO: 13 / SEQ ID NO: 14 | 2.18E+05 | 1.44E-03 | 6.66 | 2.20E+05 | 8.50E-04 | 3.89 | - |

PD-1 BINDING DOMAINS

FIELD

The present disclosure relates to the field of antibodies. In particular it relates to the field of therapeutic antibodies for the treatment of diseases involving aberrant cells. More in particular it relates to novel binding domains that bind to human PD-1, and to binding moieties comprising such binding domain.

BACKGROUND

Cancer is still a major cause of death in the world, in spite of the many advances that have been made in the treatment of the disease and the increased knowledge of the molecular events that lead to cancer. Traditionally, most cancer drug discovery has focused on agents that block essential cell functions and kill dividing cells. However, in cases of advanced cancer, no matter how aggressively applied, even to the point where patients suffer life-threatening side-effects from the treatment, chemotherapy rarely results in a complete cure. In most cases the tumors in the patients stop growing or temporarily shrink (referred to as remission) only to start proliferating again, sometimes more rapidly (referred to as relapse), and become increasingly more difficult to treat. Over the past years, the focus of cancer drug development has moved away from broadly cytotoxic chemotherapy to targeted cytostatic therapies with less toxicity. Treatment of advanced cancer with targeted therapies has been validated clinically in leukemia and some other cancers. However, in a majority of carcinomas, targeted approaches are still proving not effective enough to completely abolish cancer in the majority of the patients.

Targeting of cancers has been achieved using a variety of different methods including for instance small molecules directed towards signaling proteins on which the cancer depends for survival and/or growth; vaccines with tumor specific proteins; cell therapies with immune cells that actively kill tumor cells, and antibodies that target cytotoxic molecules to the tumor; interfere with signaling and/or that (re)direct the immune system of the host to the tumor cells.

Immune checkpoint proteins, like for instance PD-1, PD-L1, CTLA-4, LAG-3, and TIM-3, are an interesting target for antibody therapy. To date, a number of monospecific antibodies targeting PD-1 have been described, as well as certain bispecific antibodies comprising a PD-1 targeting binding domain. However, each of these antibodies has its own challenges in the production of an effective therapeutic drug. There thus remains a need for the development of novel PD-1 binding domains in order to produce effective PD-1 targeting therapeutic antibodies.

SUMMARY

One of the objects of the present disclosure is to provide a new pharmaceutical agent for the treatment of human disease, in particular for the treatment of cancer. This object is met by the provision of novel anti-human PD-1 binding domains, and in particular by binding moieties, such as antibodies, comprising such anti-human PD-1 binding domains.

In certain embodiments, the present disclosure provides an anti-human PD-1 binding domain having higher binding affinity for human PD-1 than a reference anti-human PD-1 binding domain, wherein the reference anti-human PD-1 binding domain comprises a heavy chain variable region having an amino acid sequence as set forth in SEQ ID NO: 20 and a light chain variable region having an amino acid sequence as set forth in SEQ ID NO: 21.

In certain embodiments, the present disclosure provides an anti-human PD-1 binding domain, which when monovalently present in a bivalent antibody, provides at least comparable, or equal or higher, potency in blocking ligand binding to PD-1 than a reference anti-human PD-1 antibody, wherein the reference anti-human PD-1 antibody comprises two heavy chain variable regions having an amino acid sequence as set forth in SEQ ID NO: 20 and two light chain variable regions having an amino acid sequence as set forth in SEQ ID NO: 21.

In certain embodiment, the present disclosure provides a binding moiety comprising a PD-1 binding domain as described herein, and in particular a monospecific or multispecific binding moiety, such as a monospecific or multispecific antibody, comprising such PD-1 binding domain.

In certain embodiment, the present disclosure provides a pharmaceutical composition comprising an effective amount of an anti-human PD-1 binding domain or binding moiety as described herein.

In certain embodiments, the present disclosure provides for a PD-1 binding domain, binding moiety comprising the PD-1 binding domain, and pharmaceutical composition as described herein, for use (a) in therapy, or (b) in the treatment of a disease associated with a suppressed immune system, or c) in the treatment of cancer.

In certain embodiments, the present disclosure provides a method for treating a disease, comprising administering an effective amount of a PD-1 binding domain, a binding moiety comprising a PD-1 binding domain, or pharmaceutical composition, as described herein, to an individual in need thereof.

In certain embodiments, the present disclosure provides a method for treating cancer, comprising administering an effective amount of a PD-1 binding domain, a binding moiety comprising a PD-1 binding domain, or pharmaceutical composition, as described herein, to an individual in need thereof.

In certain embodiments, the present disclosure provides a nucleic acid sequence encoding the heavy chain variable region of an anti-human PD-1 binding domain as described herein, a vector and cell comprising such nucleic acid sequence, and a cell producing an anti-human PD-1 binding domain, or the binding moiety, as described herein.

In certain embodiments, the present disclosure provides a method for producing an anti-human PD-1 binding domain as described herein, as well as a method for producing variants thereof.

DETAILED DESCRIPTION

In certain embodiments, the present disclosure provides several anti-human PD-1 binding domains, the heavy chain variable region having an amino acid sequence as set forth in SEQ ID NO: 1-9. In certain embodiments, the anti-human PD-1 binding domain comprises a heavy chain variable region, wherein the heavy chain variable region comprises the heavy chain CDR1 (HCDR1), heavy chain CDR2 (HCDR2), and heavy chain CDR3 (HCDR3) of any one of the heavy chain variable regions having an amino acid sequence as set forth in SEQ ID NO: 1-9.

Programmed Cell Death 1 protein (PD-1) is a cell surface receptor that belongs to the CD28 family of receptors and is expressed on T cells and pro-B cells. PD-1 is presently known to bind two ligands, PD-L1 and PD-L2. PD-1, functioning as an immune checkpoint, plays an important role in down regulating the immune system by inhibiting the activation of T-cells, which in turn reduces autoimmunity and promotes self-tolerance. The inhibitory effect of PD-1 is thought to be accomplished through a dual mechanism of promoting apoptosis (programmed cell death) in antigen specific T-cells in lymph nodes while simultaneously reducing apoptosis in regulatory T cells (suppressor T cells). PD-1 is also known under a number of different aliases such as PDCD1; Programmed Cell Death 1; Systemic Lupus Erythematosus Susceptibility 2; Protein PD-1; HPD-1; PD1; Programmed Cell Death 1 Protein; CD279 Antigen; CD279; HPD-L; HSLE1; SLEB2; and PD-1. External Ids for PD-1 are HGNC: 8760; Entrez Gene: 5133; Ensembl: ENSG00000188389; OMIM: 600244; and UniProtKB: Q15116. New classes of drugs that block the activity of PD-1, the PD-1 inhibitors, activate the immune system to attack tumors and are therefore used with a certain level of success to treat some types of cancer.

In certain embodiments, the anti-human PD-1 binding domain comprises at least a heavy chain variable region and a light chain variable region. The light chain variable region can be any suitable light chain variable region as described further herein. In certain embodiments, the light chain variable region preferably is a light chain variable region of a light chain that is capable of pairing with multiple heavy chains having different epitope specificities. Such light chain is also referred to in the art as a "common light chain". In certain embodiments, the present disclosure provides an anti-human PD-1 binding domain having higher binding affinity for human PD-1 than a reference anti-human PD-1 binding domain, wherein the reference anti-human PD-1 binding domain comprises a heavy chain variable region having an amino acid sequence as set forth in SEQ ID NO: 20 and a light chain variable region having an amino acid sequence as set forth in SEQ ID NO: 21.

In certain embodiments, the present disclosure provides a bivalent monospecific binding moiety comprising anti-human PD-1 binding domains; wherein the binding moiety has higher binding affinity for human PD-1 than a reference anti-human PD-1 antibody, wherein the reference anti-human PD-1 antibody comprises two heavy chain variable regions having an amino acid sequence as set forth in SEQ ID NO: 20 and two light chain variable regions having an amino acid sequence as set forth in SEQ ID NO: 21, such as monospecific PD-1 antibody nivolumab or a monospecific PD-1 antibody comprising the variable regions of nivolumab.

Determining if an anti-human PD-1 binding domain has a higher binding affinity for human PD-1 than the reference anti-human PD-1 binding domain can be done by measuring the binding affinity of both anti-human PD-1 binding domains in the same type of assay, using the same assay conditions. Thus, in certain embodiments, the binding affinity of the anti-human PD-1 binding domain or of the bivalent monospecific binding moiety, and the binding affinity of the reference anti-human PD-1 binding domain or of the reference anti-human PD-1 antibody, are measured in the same type of assay, using the same assay conditions. In certain embodiments, the assay is an assay that uses surface plasmon resonance (SPR) to measure binding affinity, such as the biosensor system of Biacore®, or Solution Equilibrium Titration (SET) (see Friguet B et al, (1985) J. Immunol Methods; 77(2): 305-319, and Hanel C et al. (2005) Anal Biochem; 339(1): 182-184). The binding affinity values of the PD-1 binding domains or of the bivalent monospecific binding moieties as provided herein are obtained with the method described in Example 3. In brief, Example 3 describes performing SPR using a Biacore 8K instrument at 25° C. Anti-human Fc antibodies are immobilized via amine coupling on flow cells of an S series sensor chip CM5 with immobilization levels of ~9000 RU. The desired capturing level (100-150 RU) of anti-PD-1 antibodies is achieved by flowing pre-determined concentration of anti-PD-1 antibodies through the active flow cell of each channel for 60 seconds with 10 μL/min flow rate. A PD-1 three-fold serial dilution concentration series (total 7 concentrations, highest at 300 nM) and running buffer is injected for 240 seconds (association time) immediately followed by running buffer for 480 seconds (dissociation time) at a flow rate of 45 μL/min. Surface is regenerated with 30-second injection of 3 M $MgCl_2$ with 30 μL/min flow rate. Binding kinetics and affinity parameters are obtained from a global fit of the data to 1 to 1 binding model.

Preferably, SPR is performed with the anti-human PD-1 binding domains in an IgG format, measuring the binding affinity of the monovalent interaction with PD-1.

In certain embodiments, the anti-human PD-1 binding domain or the bivalent monospecific binding moiety has at least a ten-fold higher binding affinity for human PD-1 than the reference anti-human PD-1 binding domain or reference anti-human PD-1 antibody, as measured by SPR as described herein. In certain embodiments, the anti-human PD-1 binding domain or the bivalent monospecific binding moiety has a ten to fifty, ten to forty, ten to thirty, or ten to twenty, fold higher binding affinity for human PD-1 than the reference anti-human PD-1 binding domain or reference anti-human PD-1 antibody, as measured by SPR as described herein. In certain embodiments, the anti-human PD-1 binding domain or the bivalent monospecific binding moiety has a ten-fold higher binding affinity for human PD-1 than the reference anti-human PD-1 binding domain or reference anti-human PD-1 antibody, as measured by SPR as described herein.

In certain embodiments, the anti-human PD-1 binding domain or the bivalent monospecific binding moiety has a binding affinity for human PD-1 in a range of about 0.1-1.0 nM, in particular in a range of about 0.3-0.8 nM, more in particular in a range of about. 0.38-0.78 nM, as measured by SPR as described herein. In certain embodiments, the anti-human PD-1 binding domain or the bivalent monospecific binding moiety has a binding affinity for human PD-1 in a range of 0.1-1.0 nM, in particular in a range of 0.3-0.8 nM, more in particular in a range of 0.38-0.78 nM, as measured by SPR as described herein. In certain embodiments, the binding affinity is the binding affinity of a monovalent interaction with PD-1.

In certain embodiments, the binding affinity is measured with both the anti-human PD-1 binding domain of the present disclosure and the reference anti-human PD-1 binding domain in a bivalent monospecific IgG format. In certain embodiments, the binding affinity is measured with both the anti-human PD-1 binding domain of the present disclosure and the reference anti-human PD-1 binding domain in a bivalent bispecific IgG format. In certain embodiments, the binding affinity is measured with the anti-human PD-1 binding domain of the present disclosure in a bivalent bispecific IgG format and the reference anti-human PD-1 binding domain in a bivalent monospecific IgG format. A bivalent bispecific IgG format may for instance comprise a PD-1 binding domain of the present disclosure, or a reference anti-human PD-1 binding domain, and a binding domain that binds an arbitrarily selected, unrelated target.

The present disclosure also provides an anti-human PD-1 binding domain, which when monovalently present in a bivalent antibody, provides at least comparable, or equal or higher, potency in blocking ligand binding to PD-1 than a reference anti-human PD-1 antibody, wherein the reference anti-human PD-1 antibody comprises two heavy chain variable regions having an amino acid sequence as set forth in SEQ. ID NO: 20 and two light chain variable regions having an amino acid sequence as set forth in SEQ ID NO: 21.

The present disclosure also provides a bivalent monospecific anti-human PD-1 binding moiety having at least comparable, or equal or higher, potency in blocking ligand binding to PD-1 than a reference anti-human PD-1 antibody, wherein the reference anti-human PD-1 antibody comprises two heavy chain variable regions having an amino acid sequence as set forth in SEQ. ID NO: 20 and two light chain variable regions having an amino acid sequence as set forth in SEQ ID NO: 21.

Determining if an anti-human PD-1 binding domain or bivalent monospecific anti-human PD-1 binding moiety provides a comparable, or equal or higher, potency in blocking ligand binding to PD-1 than the reference anti-human PD-1 antibody can be done by measuring the potency of both the anti-human PD-1 binding domain or moiety and the reference anti-human PD-1 antibody in the same type of assay, using the same assay conditions. Thus, in certain embodiments, the potency in blocking ligand binding to PD-1 of the anti-human PD-1 binding domain or of the bivalent monospecific binding moiety, and the potency in blocking ligand binding to PD-1 of the reference anti-human PD-1 antibody, are measured in the same type of assay, using the same assay conditions. In certain embodiments, the assay is a PD-1/PD-L1 reporter assay. The potency data of the PD-1 binding domains or of the binding moieties comprising the PD-1 binding domains provided herein is obtained with the PD-1/PD-L1 reporter assay as described in Example 2.

In brief, the PD-1/PD-L1 reporter assay described in Example 2 is performed using PD-L1 aAPC/CHO-K1 cells, which are CHO-K1 cells expressing human PD-L1 and an engineered cell surface protein designed to activate cognate TCRs in an antigen-independent manner, and Jurkat T cells expressing human PD-1 and a luciferase reporter driven by an NFAT response element (NFAT-RE). Assay plates comprising the PD-L1 cells or PBS are incubated overnight at 37° C., 5% $CO_2$ and 95% Relative Humidity. After incubation, wells are emptied and test and control IgG added in serial dilution, starting with 10 μg/ml and performing 6-step 4-fold titration. A basal control, which is control without IgG is also prepared. IgGs of which activities need to be compared directly are incubated on same plate. Jurkat T cells are added, and assay plates are incubated for 6 hours at 37° C., 5% $CO_2$ and 95% Relative Humidity. Following 6 hours of incubation, plates are left at room temperature for 10 min, and luciferase activity is measured.

Preferably, the anti-human PD-1 binding domain of the present disclosure and the reference anti-human PD-1 antibody are used at the same concentration, preferably both in bivalent monospecific IgG format.

In certain embodiments, a comparable potency in PD-1—ligand blocking activity is a potency within a 5 fold range of the potency in blocking ligand binding to PD-1 of the reference anti-human PD-1 binding domain or anti-human PD-1 binding moiety, and includes a 5, 4, 3, and 2 fold, preferably a 3 fold, deviation, from the potency in blocking ligand binding to PD-1 of the reference anti-human PD-1 antibody.

In certain embodiments, a higher potency in PD-1—ligand blocking activity is a potency that is a 5, 4, 3, or 2 fold, preferably a 3 fold, higher potency than the potency in blocking ligand binding to PD-1 of the reference anti-human PD-1 antibody. In certain embodiments, a higher potency in PD-1 ligand blocking activity is a potency that is a 1.1-2.0 fold, preferably a 1.2-1.8 or 1.2-1.6 fold, more preferably a 1.2-1.4 fold, higher potency than the potency in blocking ligand binding to PD-1 of the reference anti-human PD-1 antibody.

The reference anti-human PD-1 binding domain is the PD-1 binding domain of a nivolumab analog antibody, preferably produced using the same production method as the 1.0 anti-human PD-1 binding domain subject to comparison. The reference anti-human PD-1 antibody is a nivolumab analog antibody, preferably produced using the same production method as the bivalent monospecific binding moiety comprising an anti-human PD-1 binding domain subject to comparison. A nivolumab analog antibody has the same heavy chain variable region sequence (SEQ ID NO: 20) as nivolumab. A nivolumab analog antibody has the same light chain variable region sequence (SEQ ID NO: 21) as nivolumab.

In certain embodiments, the anti-human PD-1 binding domain comprises a heavy chain variable region, wherein the heavy chain variable region comprises the heavy chain CDR1. (HCDR1), heavy chain CDR2 (HCDR2), and heavy chain CDR3 (HCDR3) of one of the heavy chain variable regions having an amino acid sequence as set forth in SEQ ID NO: 1-9.

CDR sequences can be defined using different methods, including, but not limited to, according to the Kabat numbering scheme (Kabat et al., J. Biol. Chem. 252:6609-6616 (1977); and/or Kabat et al., U.S. Dept. of Health and Human Services, "Sequences of proteins of immunological interest" (1991)), the Chothia numbering scheme (Chothia et al, J. Mol. Biol. 196:901-917 (1987); Chothia et al., Nature 342: 877-883, 1989; and/or Al-Lazikani B. et al., J. Mol. Biol., 273: 927-948 (1997)), the numbering system of Honegger and Plukthun (Honegger and Plückthun, J. Mol. Biol., 309:657-670 (2001)), the numbering system of MacCallum (MacCallum et al., J. Mol. Biol. 262:732-745 (1996); and/or Abhinandan and Martin, Mol. Immunol., 45: 3832-3839 (2008)), the numbering system of Lefranc (Lefranc M. P. et al, Dev. Comp. Immunol., 27: 55-77 (2003); and/or Honegger and Plückthun, J. Mol. Biol., 309:657-670 (2001)), or according to IMGT (discussed in Giudicelli et al., Nucleic Acids Res. 25: 206-21 1 (1997)).

Each of these numbering schemes base their definition of CDRs on a predicted contribution of amino acid residues in the heavy or light chain variable region to antigen binding. Hence, each method to identify CDRs can be used to identify the CDRs of the binding domains of the present disclosure. In certain embodiments, the heavy chain CDRs of a binding domain of the present disclosure is according to Kabat, Chothia, or IMGT. In certain embodiments, the heavy chain CDRs of a binding domain of the present disclosure is according to Kabat. In certain embodiments, the heavy chain CDRs of a binding domain of the present disclosure is according to Chothia. In certain embodiments; the heavy chain CDRs of a binding domain of the present disclosure is according to IMGT.

In certain embodiments, the anti-human PD-1 binding domain comprises a heavy chain variable region, wherein the heavy chain variable region comprises a heavy chain CDR1 (HCDR1) from a heavy chain variable region having an amino acid sequence from the group consisting of SEQ NO: 1-9; a heavy chain CDR2 (HCDR2) from a heavy chain variable region having an amino acid sequence from the group consisting of SEQ ID NO:1-9; and a heavy chain CDR3 (HCDR3) from a heavy chain variable region having an amino acid sequence from the group consisting of SEQ ID NO: 1-9.

The HCDRs according to Kabat are indicated in bold and underlined in the list of sequences provided herein.

In certain embodiments, the heavy chain variable region of the anti-human PD-1 binding domain comprises:
heavy chain CDR1 (HCDR1), heavy chain CDR2 (HCDR2), and heavy chain CDR3 (HCDR3), having an amino acid sequence as set forth in SEQ ID NO: 22, SEQ ID NO: 23, and SEQ ID NO: 24; respectively;
heavy chain CDR1 (HCDR1), heavy chain CDR2 (HCDR2), and heavy chain CDR3 (HCDR3), having an amino acid sequence as set forth in SEQ ID NO: 25; SEQ ID NO: 26, and SEQ ID NO: 27, respectively;
heavy chain CDR1 (HCDR1), heavy chain CDR2 (HCDR2), and heavy chain CDR3 (HCDR3), having an amino acid sequence as set forth in SEQ ID NO: 28, SEQ ID NO: 29, and SEQ ID NO: 30; respectively;
heavy chain CDR1 (HCDR), heavy chain CDR2 (HCDR2), and heavy chain CDR3 (HCDR3), having an amino acid sequence as set forth in SEQ ID NO: 31, SEQ ID NO: 32, and SEQ ID NO: 33, respectively;
heavy chain CDR1 (HCDR1), heavy chain CDR2 (HCDR2), and heavy chain CDR3 (HCDR3), having an amino acid sequence as set forth in SEQ ID NO: 34, SEQ ID NO: 35, and SEQ ID NO: 36, respectively;
heavy chain CDR1 (HCDR1), heavy chain CDR2 CDR2), and heavy chain CDR3 (HCDR3), having an amino acid sequence as set forth in SEQ ID NO: 37, SEQ ID NO: 38, and SEQ ID NO: 39, respectively;
heavy chain CDR1 (HCDR1), heavy chain CDR2 (HCDR2), and heavy chain CDR3 (HCDR3), having an amino acid sequence as set forth in SEQ ID NO: 40, SEQ ID NO: 41, and SEQ ID NO: 42, respectively;
heavy chain CDR1 (HCDR1), heavy chain CDR2. (HCDR2), and heavy chain CDR3 (HCDR3), having an amino acid sequence as set forth in SEQ ID NO: 43, SEQ ID NO: 44, and SEQ ID NO: 45, respectively; or
heavy chain CDR1 (HCDR1), heavy chain CDR2 (HCDR2), and heavy chain CDR3 (HCDR3), having an amino acid sequence as set forth in SEQ ID NO: 46, SEQ ID NO: 47, and SEQ ID NO: 48, respectively;
wherein each of the HCDRs may comprise al most three, two, or one amino acid substitution.

In certain embodiments, the heavy chain variable region of the anti-human PD-1 binding domain comprises:
heavy chain CDR1 (HCDR1), heavy chain CDR2 (HCDR2), and heavy chain CDR3 (HCDR3), having an amino acid sequence as set forth in SEQ ID NO: 22. SEQ ID NO: 23, and SEQ ID NO: 24, respectively;
heavy chain CDR1 (HCDR), heavy chain CDR2 (HCDR2), and heavy chain CDR3 (HCDR3), having an amino acid sequence as set forth in SEQ ID NO: 25. SEQ ID NO: 26, and SEQ ID NO: 27, respectively;
heavy chain CDR1 (HCDR1), heavy chain CDR2 (HCDR2), and heavy chain CDR3 (HCDR3), having an amino acid sequence as set forth in SEQ ID NO: 28, SEQ ID NO: 29, and SEQ ID NO: 30, respectively;
heavy chain CDR1 (HCDR1), heavy chain CDR2 (HCDR2), and heavy chain CDR3 (HCDR3), having an amino acid sequence as set forth in SEQ ID NO: 31, SEQ ID NO: 32, and SEQ ID NO: 33, respectively;
heavy chain CDR1 (HCDR1), heavy chain CDR2 (HCDR2), and heavy chain CDR3 (HCDR3), having an amino acid sequence as set forth in SEQ ID NO: 34, SEQ ID NO: 35, and SEQ ID NO: 36, respectively;
heavy chain CDR1 (HCDR1), heavy chain CDR2 (17 CDR2), and heavy chain CDR3 (HCDR3), having an amino acid sequence as set forth in SEQ ID NO: 37, SEQ ID NO: 38, and SEQ ID NO: 39, respectively;
heavy chain CDR1 (HCDR1), heavy chain CDR2 (HCDR2), and heavy chain CDR3 (HCDR3), having an amino acid sequence as set forth in SEQ ID NO: 40, SEQ ID NO: 41, and SEQ 11) NO: 42, respectively;
heavy chain CDR1 (HCDR1), heavy chain CDR2 (HCDR2), and heavy chain CDR3 (HCDR3), having an amino acid sequence as set forth in SEQ ID NO: 43, SEQ ID NO: 44, and SEQ ID NO: 45, respectively; or
heavy chain CDR1 (HCDR1), heavy chain CDR2 (HCDR2), and heavy chain CDR3 (HCDR3), having an amino acid sequence as set forth in SEQ ID NO: 46, SEQ ID NO: 47, and SEQ ID NO: 48, respectively.

In certain embodiments, a PD-1 binding domain of the present disclosure also includes PD-1 binding domain variants, wherein each of the HCDRs may comprise at most three, two, or one amino acid substitution. In certain embodiments, only one or two HCDRs may comprise al most three; two, or one amino acid substitution.

For example, suitable positions for introducing an amino acid variation include, but are not limited to, the first, second, and/or fourth amino acid of HCDR1; the third, seventh, eighth, ninth, tenth, eleventh, thirteenth, fourteenth, and/or sixteenth amino acid of HCDR2: and/or the sixth and/or thirteenth amino acid of HCDR3. CDR sequences according to Rabat are indicated in bold and underlined in the list of sequences provided herein.

In certain embodiments, the present disclosure thus also provides an anti-human PD-1 binding domain comprising:
HCDR1 having amino acid sequence $X_1X_2FX_3S$, wherein
$X_1$ can be F, Y, T, or H;
$X_2$ can be Y, Q, E, H, or D;
$X_3$ can be W, or Y; and/or
HCDR2 having amino acid sequence $YIX_1YSGX_2X_3X_4X_5X_6PX_7X_8KX_9$, wherein
$X_1$ can be Y, V, or I;
$X_2$ can be S, or G;
$X_3$ can be T, S, H, N, W, L, or Q;
$X_4$ can be S, or N;
$X_5$ can be F, V, or L;
$X_6$ can be N, or S;
$X_7$ can be S or A;
$X_8$ can be F or L;
$X_9$ can be S, T, G, D, R, or N; and/or
HCDR3 having amino acid sequence $GGYTGX_1GGDWFDX_2$, wherein
$X_1$ can be Y, H, V, or A;
$X_2$ can be P, V, Y, W, F, T, Q, H, or S.

Other suitable positions for introducing an amino acid variation include, but are not limited to, the second, third, fourth, and/or fifth amino acid of HCDR1; the third; fourth, fifth, sixth, eighth, ninth, tenth, eleventh, twelfth, thirteenth, fourteenth, fifteenth, sixteenth and/or seventeenth amino acid of HCDR2; and/or the first, second, sixth, seventh, ninth, tenth, fourteenth, fifteenth, sixteenth and/or eighteenth amino acid of HCDR3. CDR sequences according to Kabat are indicated in bold and underlined in the list of sequences provided herein.

In certain embodiments, the present disclosure thus also provides an anti-human PD-1 binding domain comprising:

HCDR1 having amino acid sequence $RX_1X_2X_3X_4$, wherein
  $X_1$ can be F, or Y;
  $X_2$ can be T, A, or V;
  $X_3$ can be M, L, or V;
  $X_4$ can be S, H, N, V, or T; and/or
HCDR2 having amino acid sequence $WIX_1X_2X_3X_4GX_5X_6X_7X_8X_9X_{10}X_{11}X_{12}X_{13}X_{14}$, wherein
  $X_1$ can be N, or D;
  $X_2$ can be P, S, or T;
  $X_3$ can be N, or Q;
  $X_4$ can be T, or D;
  $X_5$ can be N, S, T, K, L, or E;
  $X_6$ can be P, Y, A, H, or F;
  $X_7$ can be T, or S;
  $X_8$ can be Y, F, or H
  $X_9$ can be A, G, V, or F;
  $X_{10}$ can be Q, R, N, L, T, or S;
  $X_{11}$ can be D, A, G, or S;
  $X_{12}$, can be F, V, or A;
  $X_{13}$ can be T, K, H, G;
  $X_{14}$ can be G, N, E, or D; and/or
HCDR3 having amino acid sequence $X_1X_2GYCX_3X_4DX_5CYPNX_6X_7X_8DX_9$, wherein
  $X_1$ can be I, S, or V;
  $X_2$ can be L, Q, or N;
  $X_3$ can be N, G, S, or D;
  $X_4$ can be I, S, P, N, or E;
  $X_5$ can be N, or I;
  $X_6$ can be W, G, Q, H, W, A, or L;
  $X_7$ can be I, V, or L;
  $X_8$ can be F, L, or I;
  $X_9$ can be Y, S, N, I, R, H, V, T, K, A, or L.

In certain embodiments, the anti-human PD-1 binding domain of the present disclosure comprises a heavy chain variable region having an amino acid sequence as set forth in any one of SEQ ID NO: 1-9, or having at least 80%, preferably 85%, more preferably 90%, or most preferably 95% sequence identity thereto.

In certain embodiments, a PD-1 binding domain of the present disclosure also includes PD-1 binding domain variants, which, in addition to the variations in the HCDRs referred to above, comprise one or more variations in the framework regions. In certain embodiments, a PD-1 binding domain variant of the present disclosure comprises no variations in the CDR regions but comprises one or more variations in the framework regions. Such variants have at least 80%, preferably 85%, more preferably 90%, or most preferably 95% sequence identity to the sequences disclosed herein, and are expected to retain PD-1 binding specificity. Thus, in certain embodiments, a PD-1 binding domain of the present disclosure comprises:

a heavy chain variable region having at least 80%, preferably 85%, more preferably 90%, or most preferably 95% sequence identity to the amino acid sequence as set forth in SEQ ID NO: 1, which heavy chain variable region comprises a HCDR1 amino acid sequence as set forth in SEQ ID NO: 25; a HCDR2 amino acid sequence as set forth in SEQ ID NO: 26; and a HCDR3 amino acid sequence as set forth in SEQ ID NO: 27;

a heavy chain variable region having at least 80%, preferably 85%, more preferably 90%, or most preferably 95% sequence identity to the amino acid sequence as set forth in SEQ ID NO: 2, which heavy chain variable region comprises a HCDR1 amino acid sequence as set forth in SEQ ID NO: 28; a HCDR2 amino acid sequence as set forth in SEQ ID NO: 29; and a HCDR3 amino acid sequence as set forth in SEQ ID NO: 30;

a heavy chain variable region having at least 80%, preferably 85%, more preferably 90%, or most preferably 95% sequence identity to the amino acid sequence as set forth in SEQ ID NO: 3, which heavy chain variable region comprises a HCDR1 amino acid sequence as set forth in SEQ ID NO: 31; a HCDR2 amino acid sequence as set forth in SEQ ID NO: 32; and a HCDR3 amino acid sequence as set forth in SEQ ID NO: 33;

a heavy chain variable region having at least 80%, preferably 85%, more preferably 90%, or most preferably 95% sequence identity to the amino acid sequence as set forth in SEQ ID NO: 4, which heavy chain variable region comprises a HCDR1 amino acid sequence as set forth in SEQ ID NO: 34; a HCDR2 amino acid sequence as set forth in SEQ ID NO: 35; and a HCDR3 amino acid sequence as set forth in SEQ ID NO: 36;

a heavy chain variable region having at least 80%, preferably 85%, more preferably 90%, or most preferably 95% sequence identity to the amino acid sequence as set forth in SEQ ID NO: 5, which heavy chain variable region comprises a HCDR1 amino acid sequence as set forth in SEQ ID NO: 37; a HCDR2 amino acid sequence as set forth in SEQ ID NO: 38; and a HCDR3 amino acid sequence as set forth in SEQ ID NO: 39;

a heavy chain variable region having at least 80%, preferably 85%, more preferably 90%, or most preferably 95% sequence identity to the amino acid sequence as set forth in SEQ ID NO: 6, which heavy chain variable region comprises a HCDR1 amino acid sequence as set forth in SEQ ID NO: 40; a HCDR2 amino acid sequence as set forth in SEQ ID NO: 41; and a HCDR3 amino acid sequence as set forth in SEQ ID NO: 42;

a heavy chain variable region having at least 80%, preferably 85%, more preferably 90%, or most preferably 95% sequence identity to the amino acid sequence as set forth in SEQ ID NO: 7, which heavy chain variable region comprises a HCDR1 amino acid sequence as set forth in SEQ ID NO: 43; a HCDR2 amino acid sequence as set forth in SEQ ID NO: 44; and a HCDR3 amino acid sequence as set forth in SEQ ID NO: 45;

a heavy chain variable region having at least 80%, preferably 85%, more preferably 90%, or most preferably 95% sequence identity to the amino acid sequence as set forth in SEQ ID NO: 8, which heavy chain variable region comprises a HCDR1 amino acid sequence as set forth in SEQ ID NO: 46; a HCDR2 amino acid sequence as set forth in SEQ ID NO: 47; and a HCDR3 amino acid sequence as set forth in SEQ ID NO: 48; or a heavy chain variable region having at least 80%, preferably 85%, more preferably 90%, or most preferably 95% sequence identity to the amino acid sequence as set forth in SEQ ID NO: 9, which heavy chain variable region comprises a HCDR1 amino acid sequence as set forth in SEQ ID NO: 22; a HCDR2 amino acid sequence as set forth in SEQ ID NO: 23; and a HCDR3 amino acid sequence as set forth in SEQ 1:13 NO: 24.

In certain embodiments, a PD-1 binding domain of the present disclosure comprises a light chain variable region. An example of a suitable light chain variable region is a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively, wherein each of the LCDRs may comprise at most three, two, or one amino acid substitution. In certain embodiments, a suitable light chain variable region is a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively. In certain embodiments, such light chain variable region may comprise a light chain variable region having an amino acid sequence as set forth in SEQ ID NO: 16, or having at least 80%, preferably 85%, more preferably 90%, or most preferably 95% sequence identity thereto. A light chain or light chain variable region comprising these LCDRs and/or light chain variable region is the light chain referred to in the art as VK1-39/JK1. This is a common light chain.

In certain embodiments, a PD-1 binding domain of the present disclosure comprises a light chain variable region having at least 80%, preferably 85%, more preferably 90%, or most preferably 95% sequence identity to the amino acid sequence as set forth in SEQ ID NO: 16, which light chain variable region comprises a LCDR1 amino acid sequence as set forth in SEQ ID NO: 49; a LCDR2 amino acid sequence as set forth in SEQ ID NO: 50; and a LCDR3 amino acid sequence as set forth in SEQ ID NO: 51.

The term 'common light chain' according to the invention refers to a light chain that is capable of pairing with multiple different heavy chains, i.e. heavy chains having different antigen or epitope binding specificities. A common light chain is particularly useful in the generation of, for instance, bispecific antibodies, where antibody production is more efficient when both binding domains comprise the same light chain. The term "common light chain" encompasses light chains that are identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like.

Apart from a common light chain comprising the LCDRs and/or light chain variable region referred to above, other common light chains known in the art may be used. Examples of such common light chains include, but are not limited to: VK1-39/JK5, comprising a light chain variable region comprising a light chain CDR1 (LCDR1), light chain CDR2 (LCDR2), and light chain CDR3 (LCDR3), of a light chain variable region having an amino acid sequence as set forth in SEQ ID NO: 52. The LCDRs according to IMGT are indicated in bold and underlined therein. In certain embodiments, the light chain comprises a light chain variable region comprising a light chain CDR1 (LCDR1), light chain CDR2 (LCDR2), and light chain CDR3 (LCDR3), of a light chain variable region having an amino acid sequence as set forth in SEQ ID NO: 52, wherein each of the LCDRs may comprise at most three, two, or one amino acid substitution. In certain embodiments, the light chain comprises a light chain variable region having an amino acid sequence as set forth in SEQ ID NO: 52, or having at least 80%, preferably 85%, more preferably 90%, or most preferably 95% sequence identity thereto; VK3-15/JK1, comprising a light chain variable region comprising a light chain CDR1 (LCDR1), light chain CDR2 (LCDR2), and light chain CDR3 (LCDR3), of a light chain variable region having an amino acid sequence as set forth in SEQ ID NO: 53. The LCDRs according to IMGT are indicated in bold and underlined therein. In certain embodiments, the light chain comprises a light chain variable region comprising a light chain CDR1 (LCDR1), light chain CDR2 (LCDR2), and light chain CDR3 (LCDR3), of a light chain variable region having an amino acid sequence as set forth in SEQ ID NO: 53, wherein each of the LCDRs may comprise at most three, two, or one amino acid substitution. In certain embodiments, the light chain comprises a light chain variable region having an amino acid sequence as set forth in SEQ ID NO: 53, or having at least 80%, preferably 85%, more preferably 90%, or most preferably 95% sequence identity thereto; VK3-20/JK1, comprising a light chain variable region comprising a light chain CDR1 (LCDR1), light chain CDR2 (LCDR2), and light chain CDR3 (LCDR3), of a light chain variable region having an amino acid sequence as set, forth in SEQ ID NO: 54. The LCDRs according to IMGT are indicated in bold and underlined therein. In certain embodiments, the light chain comprises a light chain variable region comprising a light chain CDR1 (LCDR1), light chain CDR2 (LCDR2), and light chain CDR3 (LCDR3), of a light chain variable region having an amino acid sequence as set forth in SEQ ID NO: 54, wherein each of the LCDRs may comprise at most three, two, or one amino acid substitution. In certain embodiments, the light chain comprises a light chain variable region having an amino acid sequence as set forth in SEQ ID NO: 54, or having at least 80%, preferably 85%, more preferably 90%, or most preferably 95% sequence identity thereto; and VL3-2I/JL3, comprising a light chain variable region comprising a light chain CDR1 (LCDR1), light chain CDR2 (LCDR2), and light chain CDR3 (LCDR3), of a light chain variable region having an amino acid sequence as set forth in SEQ ID NO: 55. The LCDRs according to IMGT are indicated in bold and underlined therein. In certain embodiments, the light chain comprises a light chain variable region comprising a light chain CDR1 (LCDR1), light chain CDR2 (LCDR2), and light chain CDR3 (LCDR3), of a light chain variable region having an amino acid sequence as set forth in SEQ ID NO: 55, wherein each of the LCDRs may comprise at most three, two, or one amino acid substitution. In certain embodiments, the light chain comprises a light chain variable region having an amino acid sequence as set forth in SEQ ID NO: 55, or having at least 80%, preferably 85%, more preferably 90%, or most preferably 95% sequence identity thereto.

VK1-39 is short for Immunoglobulin Variable Kappa 1-39 Gene. The gene is also known as Immunoglobulin Kappa Variable 1-39; IGKV139; IGKV1-39; IgV$_K$1-39. External Ids for the gene are HGNC: 5740; Entrez Gene: 28930; Ensembl: ENSG00000242371. A preferred amino acid sequence for VK1-39 is given as SEQ ID NO: 56. This is the sequence of the V-region. The V-region can be combined with one of five J-regions. Two preferred joined sequences are indicated as VK1-39/JK1 and VK1-39/JK5; alternative names are IgV$_K$1-39*01/IGJ$_K$1*01 or IgV$_K$1-39*01/IGJ$_K$5*01 (nomenclature according to the IMGT database). These names are exemplary and encompass allelic variants of the gene segments.

VK3-15 is short for Immunoglobulin Variable Kappa 3-15 Gene. The gene is also known as Immunoglobulin Kappa Variable 3-15; IGKV315; IGKV3-15; IgV$_K$3-15. External Ids for the gene are HGNC: 5816; Entrez Gene: 28913; Ensembl: ENSG00000244437. A preferred amino acid sequence for VK3-15 is given as SEQ ID NO: 57. This is the sequence of the V-region. The V-region can be combined with one of five J-regions. A preferred joined sequence is indicated as VK3-15/JK1; alternative name is V$_K$3-15*01/

IGJκ1*01 (nomenclature according to the IMGT database). This name is exemplary and encompasses allelic variants of the gene segments.

VK3-20 is short for Immunoglobulin Variable Kappa 3-20 Gene. The gene is also known as Immunoglobulin Kappa Variable 3-20; IGKV320; IGKV3-20; IgVκ3-20. External Ids for the gene are HGNC: 5817; Entrez Gene: 28912; Ensembl: ENSG00000239951. A preferred amino acid sequence for VK3-20 is as SEQ ID NO: 58. This is the sequence of the V-region. The V-region can be combined with one of five J-regions. A preferred joined sequence is indicated as VK3-20/JK1; alternative name is IgVκ3-20*01/IGJκ1*01 (nomenclature according to the IMGT database). This name is exemplary and encompasses allelic variants of the gene segments.

VL3-21 is short for Immunoglobulin Variable Lambda 3-21 Gene. The gene is also known as Immunoglobulin Lambda Variable 3-21; IGLV321; IGLV3-21; IgVλ,3-21. External Ids for the gene are HGNC: 5905; Entrez Gene: 28796; Ensembl: ENSG00000211662.2. A preferred amino acid sequence for VL3-21 is given as SEQ ID NO: 59. This is the sequence of the V-region. The V-region can be combined with one of five J-regions. A preferred joined sequence is indicated as VL3-21/JL3; alternative name is IgVλ3-21/IGJλ3 (nomenclature according to the IMGT database). This name is exemplary and encompasses allelic variants of the gene segments.

Further, any light chain variable region of a PD-1 antibody available in the art may be used, or any other light chain variable region that can readily be obtained, such as from, for instance, an antibody display library by showing antigen binding activity when paired with a PD-1 binding domain of the invention.

In certain embodiments, a PD-1 binding domain of the present disclosure may further comprise a CH1 and CL region. Any CH1 domain may be used, in particular a human CH1 domain. An example of a suitable CH1 domain is provided by the amino acid sequence provided as SEQ ID NO: 17. Any CL domain may be used, in particular a human CL. An example of a suitable CL domain is provided by the amino acid sequence provided as SEQ ID NO: 60.

A PD-1 binding domain of the present disclosure can be used as a binding domain in a binding moiety. A "binding moiety" refers to a proteinaceous molecule and includes for instance all antibody formats available in the art, such as for example a full length IgG antibody, immunoconjugates, diabodies, BiTEs, Fab fragments, scFv, tandem scFv, single domain antibody (like $V_{HH}$ and $V_H$), minibodies, scFab, scFv-zipper, nanobodies, DART molecules, TandAb, FabscFv, F(ab)'2, F(ab)'2-scFv2, and intrabodies.

In one embodiment, the binding moiety of the present disclosure is a monospecific binding moiety, in particular a monospecific antibody. A monospecific antibody according to the present disclosure is an antibody, in any antibody format, that comprises one or more binding domains with specificity for a single target. In certain embodiments, a monospecific binding moiety of the present disclosure may further comprise an Fc region or a part thereof. In certain embodiments, a monospecific binding moiety of the present disclosure is an IgG1 antibody.

In one embodiment, the binding moiety of the present disclosure is a multispecific binding moiety, in particular a multispecific antibody. A multispecific antibody according to the present disclosure is an antibody, in any antibody format, that comprises at least two binding domains which have specificity for at least two different targets or epitopes. In certain embodiments, a multispecific antibody of the invention is a bispecific antibody. In certain embodiments, a multispecific antibody of the present disclosure may further comprise an Fc region or a part thereof. In certain embodiments, a multispecific antibody of the present disclosure is an IgG1 antibody.

The present disclosure further provides a nucleic acid sequence encoding the heavy chain variable region of an anti-human PD-1 binding domain or binding moiety as described herein.

Further provided herein is a vector useful for producing a PD-1 binding domain or binding moiety of the present disclosure. In certain embodiments, such expression vector comprises a polynucleotide encoding the heavy chain variable region of the anti-human PD-1 binding domain as described herein. In certain embodiments, a vector of the present disclosure may further encode a CH1 region and preferably a hinge, CH2 and CH3 region. In certain embodiments, the vector of the present disclosure may further comprise at least one polynucleotide encoding a light chain variable region, and preferably a CL region. In certain embodiments, the light chain variable region can be a common light chain variable region as described herein.

The present disclosure also provides a cell comprising a nucleic acid sequence encoding the heavy chain variable region of an anti-human PD-1 binding domain as described herein. In certain embodiments, a cell of the present disclosure may further comprises a nucleic acid sequence encoding a CH1 region and preferably a hinge, CH2 and CH3 region. In certain embodiments, a cell of the present disclosure may further comprises at least one nucleic acid sequence encoding a light chain variable region, and preferably a CL region. In certain embodiments, the light chain variable region can be a common light chain variable region as described herein.

Further provided herein is a cell producing an anti-human PD-1 binding domain or a binding moiety as described herein. In certain embodiments, such cell can be a recombinant cell, which has been transformed with a vector of the present disclosure.

Further provided herein is a method for producing an anti-human PD-1 binding domain, or a binding moiety comprising an anti-human PD-1 binding domain, of the present disclosure, wherein the method comprises culturing a cell as described herein and recovering the anti-human PD-1 binding domain, or the binding moiety comprising an anti-human PD-1 binding domain, from the cell or supernatant.

Further provided herein is a method for producing a variant of an anti-human PD-1 binding domain of the present disclosure, wherein the method comprises:
  generating a sequence variant of a heavy chain variable region as described herein;
  and
  expressing the sequence variant and a light chain variable region as described herein in a cell.

Methods for generating sequence variants are well known in the art. One can take a random approach in generating sequence variants or a targeted approach, where one can for instance aim at introducing variations that are likely to increase or decrease binding affinity. Routine methods for affinity maturing antibody binding domains are widely known in the art, see for instance Tabasinezhad M. et al. Immunol Lett. 2019; 212:106-113. One can also aim at introducing variations that mitigate developability risks with a view on producing a binding domain, or moiety comprising such binding domain, at large scale. Variations may be introduced that are likely not to cause a loss in binding specificity and/or affect binding affinity. Whether amino acid residues within the CDRs and/or framework regions can be substituted, for instance with a conservative amino acid residue, and without, or substantially without, loss in binding specificity and/or affinity, can be determined by methods well known in the art. Experimental examples include, but are not limited to, for instance, alanine scanning (Cunningham B C, Wells J A. Science. 1989; 244(4908):1081-5), and deep mutational scanning (Araya C L, Fowler D M. Trends Biotechnol, 2011; 29(9):435-42). Computational methods have also been developed that can predict the effect of amino acid variation, such as for instance described in Sruthi C K, Prakash M. PLoS One. 2020; 15(1):e0227621, Choi Y. et al, PLoS One. 2012; 7(10):e46688, and Munro D. Singh M. Bioinformatics. 2020; 36(22-23):5322-9.

Further provided herein are any variant anti-human PD-1 binding domains produced by the above described method; binding moieties, such as antibodies, comprising any of said variant binding domains; a pharmaceutical composition comprising any of said variant anti-human PD-1 binding domains or binding moieties; nucleic acids encoding any of said variant binding domains; vectors and cells comprising said nucleic acids; and use of said variant binding domains or pharmaceutical composition for the treatment of cancer.

Pharmaceutical Composition and Methods

An anti-human PD-1 binding domain of the present disclosure or a binding moiety of the present disclosure can be used in a pharmaceutical composition, together with a pharmaceutically acceptable carrier, to effectively treat a disease, preferably a disease associated with a suppressed immune system, in particular cancer. Treatment includes the administration of an effective amount of the PD-1 binding domain, binding moiety, or pharmaceutical composition, to a subject in need thereof.

In certain embodiments, the present disclosure provides an anti-human PD-1 binding domain, a binding moiety, or a pharmaceutical composition, as described herein for use in therapy.

In certain embodiments, the present disclosure provides an anti-human PD-1 binding domain, a binding moiety, or a pharmaceutical composition, as described herein for use in the treatment of a disease associated with a suppressed immune system, in particular cancer.

In certain embodiments, the present disclosure provides a method for treating a disease, wherein the method comprises administering an effective amount of an anti-human PD-1 binding domain, a binding moiety, or a pharmaceutical composition as described herein to an individual in need thereof.

In certain embodiments, the present disclosure provide a method for treating a disease associated with a suppressed immune system, in particular cancer, wherein the method comprises administering an effective amount of an anti-human PD-1 binding domain, a binding moiety, or a pharmaceutical composition as described herein to an individual in need thereof.

As used herein, the terms "individual", "subject" and "patient" are used interchangeably and refer to a mammal such as a human, mouse, rat, hamster, guinea pig, rabbit, cat, dog, monkey, cow, horse, pig and the like (e.g., a patient, such as a human patient, having cancer).

The terms "treat," "treating," and "treatment," as used herein, refer to any type of intervention or process performed on or administering an active agent or combination of active agents to a subject with the objective of curing or improving a disease or symptom thereof. This includes reversing, alleviating, ameliorating, inhibiting, or slowing down a symptom, complication, condition or biochemical indicia associated with a disease, as well as preventing the onset, progression, development, severity or recurrence of a symptom, complication, condition or biochemical indicia associated with a disease.

As used herein, "effective treatment" or "positive therapeutic response" refers to a treatment producing a beneficial effect, e.g., amelioration of at least one symptom of a disease or disorder, e.g., cancer. A beneficial effect can take the form of an improvement over baseline, including an improvement over a measurement or observation made prior to initiation of therapy according to the method. For example, a beneficial effect can take the form of slowing, stabilizing, stopping or reversing the progression of a cancer in a subject at any clinical stage, as evidenced by a decrease or elimination of a clinical or diagnostic symptom of the disease, or of a marker of cancer. Effective treatment may, for example, decrease in tumor size, decrease the presence of circulating tumor cells, reduce or prevent metastases of a tumor, slow or arrest tumor growth and/or prevent or delay tumor recurrence or relapse.

The term "therapeutic amount" or "effective amount" refers to an amount of an agent or combination of agents that provides the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In some embodiments, a therapeutic amount is an amount sufficient to delay tumor development. In some embodiments, a therapeutic amount is an amount sufficient to prevent or delay tumor recurrence.

The effective amount of the agent or composition may: (i) reduce the number of cancer cells; (ii) reduce tumor size; (iii) inhibit, retard, slow to some extent and may stop cancer cell infiltration into peripheral organs; (iv) inhibit tumor metastasis; (v) inhibit tumor growth; (vi) prevent or delay occurrence and/or recurrence of tumor; and/or (vii) relieve to some extent one or more of the symptoms associated with the cancer.

An effective amount may vary according to factors such as the disease state, age, sex, and weight of the individual to be treated, and the ability of the agent or combination of agents to elicit a desired response in the individual.

An effective amount can be administered in one or more administrations.

An effective amount also includes an amount that balances any toxic or detrimental effects of the agent or combination of agents and the therapeutically beneficial effects.

The term "agent" refers to a therapeutically active substance, in the present case a PD-1 binding domain of the present disclosure, a binding moiety of the present disclosure, or a pharmaceutical composition of the present disclosure.

General Terms

As used herein, "to comprise" and its conjugations is used in its non-limiting sense to mead that items following the word are included, but items not specifically mentioned are not excluded.

The articles "a" and "an" are used herein to refer to one or more of the grammatical object of the article. By way of example, "an element" means one or more elements.

A reference herein to a patent document or other matter is not to be taken as an admission that that document or matter was known or that the information it contains was part of the common general knowledge at the priority date of any of the claims.

All patent and literature references cited in the present specification are hereby incorporated by reference in their entirety.

Note that in the present specification, unless stated otherwise, amino acid positions assigned to CDRs and frameworks in a variable region of an antibody or antibody fragment are specified according to Kabat's numbering (see Sequences of Proteins of Immunological Interest (National Institute of Health, Bethesda, Md., 1987 and 1991)). Amino acids in the constant regions are indicated according to the EU numbering system.

Accession numbers are primarily given to provide a further method of identification of a target, the actual sequence of the protein bound may vary, for instance because of a mutation in the encoding gene such as those occurring in some cancers or the like. The antigen binding site binds the antigen and a variety of variants thereof, such as those expressed by some antigen positive immune or tumor cells.

When herein reference is made to a gene, a protein, the reference is preferably to the human form of the gene or protein. When herein reference is made to a gene or protein reference is made to the natural gene or protein and to variant forms of the gene or protein as can be detected in tumors, cancers and the like, preferably as can be detected in human tumors, cancers and the like.

HGNC stands for the HUGO Gene nomenclature committee. The number following the abbreviation is the accession number with which information on the gene and protein encoded by the gene can be retrieved from the HGNC database. Entrez Gene provides the accession number or gene ID with which information on the gene or protein encoded by the gene can be retrieved from the NCBI (National Center for Biotechnology Information) database. Ensemble provides the accession number with which information on the gene or protein encoded by the gene can be obtained from the Ensemble database. Ensembl is a joint project between EMBL-EBI and the Wellcome Trust Sanger Institute to develop a software system which produces and maintains automatic annotation on selected eukaryotic genomes.

BRIEF DESCRIPTION OF THE DRAWINGS

In the Figures, bivalent monospecific antibodies are indicated in the format SEQ ID NO: A, where SEQ ID NO: A refers to the heavy chain variable sequence of both binding domains. Each binding domain of the monospecific antibodies comprises a light chain. In the Examples, which are used to illustrate the present disclosure but are not intended to limit the disclosure in any way, each binding domain of the monospecific antibodies comprises a light chain variable region having an amino acid sequence as set forth in SEQ ID NO: 16 and a light chain constant region having an amino acid sequence as set forth in SEQ ID NO: 60. The monospecific antibodies preferably are IgG1 antibodies comprising a CH1, hinge, CH2, and CH3. In the Examples, which are used to illustrate the present disclosure but are not intended to limit the disclosure in any way, monospecific antibodies were screened in IgG1 format, wherein the PD-1 binding heavy chains comprise a CH1 having an amino acid sequence as set forth in SEQ ID NO: 17, a CH2 having an amino acid sequence as set forth in SEQ ID NO: 18, and a CH3 having an amino acid sequence as set forth in SEQ ID NO: 19.

Bivalent monospecific nivolumab analog antibody is indicated in the format SEQ ID NO: A/SEQ ID NO: B, where SEQ ID NO: A refers to the respective heavy chain sequence and SEQ ID NO: B refers to the respective light chain sequence. This reference antibody analog is used in IgG1 or IgG4 format, and each binding domain comprises a light chain.

Figure 1:
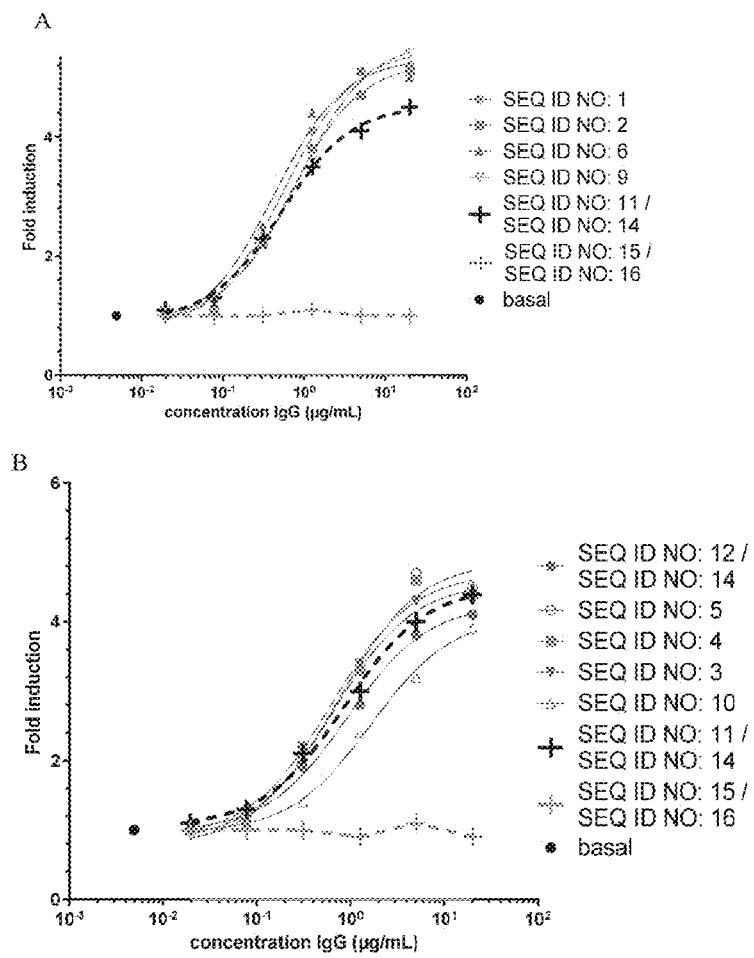

Bivalent bispecific antibodies are indicated in the format SEQ ID NO: A×Antigen A, where SEQ ID NO: A refers to the heavy chain variable sequence of the PD-1 binding domain and Antigen A refers to the heavy chain variable sequence of an unrelated; arbitrarily selected antigen. Each binding domain of the bispecific antibodies comprises a light chain. The bispecific antibodies are IgG1 antibodies, comprising a CH1, hinge, CH2, and CH3.

FIG. 1 shows the results of screening of affinity matured variants in a PD-1/PD-L1 reporter assay. A) IgG's comprising affinity matured heavy chain variable regions having an amino acid sequence as set forth in SEQ ID NO: 1. SEQ ID NO: 2, and SEQ ID NO: 6; were compared with parental antibody comprising a heavy chain variable region having an amino acid sequence as set forth in SEQ ID NO: 9, a nivolumab analog (SEQ ID NO: 11/SEQ ID NO: 14) as a positive control, and a negative control (SEQ ID NO: 15/SEQ ID NO: 16). B) IgG's comprising affinity matured heavy chain variable regions having an amino acid sequence as set forth in SEQ ID NO: 3, SEQ ID NO: 4, and SEQ ID NO: 5; were compared with parental antibody comprising a heavy chain variable region having an amino acid sequence as set forth in SEQ ID NO: 10, nivolumab analogs (SEQ ID NO: 11/SEQ ID NO: 14 and SEQ ID NO: 12/SEQ ID NO: 14) as positive controls, and a negative control (SEQ ID NO: 15/SEQ ID NO: 16).

FIG. 2 shows the binding affinity of the PD-1 binding domains comprising a heavy chain variable region having an amino acid sequence as set forth in SEQ ID NO: 1, SEQ NO: 6, or SEQ ID NO: 5, in bivalent monospecific format, compared with bivalent monospecific nivolumab analog 1 (SEQ ID NO: 11/SEQ ID NO: 14; in quadruplicate) and the PD-1 binding domain of nivolumab analog 1 as part of a bivalent bispecific antibody (SEQ ID NO: 11; SEQ ID NO: 14×SEQ ID NO: 15/SEQ ID NO: 16).

FIG. 3 shows the binding affinity of bispecific antibodies comprising SEQ ID NO: 7 and a binding domain against an arbitrarily selected antigen not impacting PD-1 binding tested in the assay, and SEQ ID NO: 8 and a binding domain against an arbitrarily selected antigen not impacting PD-1 binding tested in the assay, to human and cynomolgus PD-1, compared with a nivolumab analog (SEQ If) NO: 13/SEQ ID NO: 14).

The following Examples illustrate the present disclosure but are not intended to limit the disclosure in any way.

EXAMPLES

Example 1—Generation of Anti-Human PD-1 Binding Domains

Anti-human PD-1 binding domains can be obtained by methods known in the art, such as for instance as described in WO 2019/009728. A large panel of heavy chain variable regions were obtained by immunizing transgenic mice comprising a common IGKV1-39 light chain (MeMo® mice) with human PD-1 antigenic moieties, including the use of different forms of DNA, protein and cell-based antigen delivery. Heavy chain variable regions of SEQ ID NO: 9 and SEQ ID NO: 10 were selected for affinity maturation. This resulted in 202 affinity matured variants of which a number were selected for further characterization in a PD-1/PD-L1 reporter assay.

Example 2—Potency of PD-1 IgG

In order to confirm that the affinity matured PD-1 heavy chain variable regions in IgG format are at least as potent as their parental IgG's, affinity matured variants were screened in a PD-1/PD-L1 reporter assay. Also included in the assay were the parental anti-PD-1 IgG's, an anti-PD-1 antibody comprising the heavy chain variable region (SEQ ID NO: 11) and light chain variable region (SEQ ID NO: 14) of nivolumab (Fc-silenced IgG1 nivolumab analog 1), and an anti-PD-1 antibody comprising the heavy chain variable region (SEQ ID NO: 12) and light chain variable region (SEQ ID NO: 14) of nivolumab (IgG4 nivolumab analog 2) as positive controls, and an anti RSV-G antibody comprising the heavy chain variable region having SEQ ID NO: 0.15 and light chain variable region having SEQ ID NO: 16 as a negative control. The last 2 wells in this column were left without IgG as a basal level control.

The PD-1 PD-L1 reporter assay was performed according to manufacturer's protocol (Promega, cat. no. J1255), which uses two cell lines: PD-L1 aAPC/CHO-K1 which are CHO-K1 cells expressing human PD-L1 and an engineered cell surface protein designed to activate cognate TCRs in an antigen-independent manner (Promega, cat, no. J109A); and PD-1 effector cells: Jurkat T cells expressing human PD-1 and a luciferase reporter driven by an NFAT response element (NFAT-RE) (Promega, cat. no. J1115A).

On day 1, Cell Recovery Medium for PD-L1 cells was prepared at room temperature: 10% FBS (Sigma, cat. no. F2442) in DMEM/F12 (Life Technologies, cat. no. 21765). The required number of PD-L1 cell vials (J109A; 1 vial per 32 IgG's to be tested) were removed from the freezer, thawed quickly at 37° C. and cells transferred to a 50 nil tube. Cell Recovery Medium was slowly added to cells, 14.5 ml/vial, volume doubling per minute. Wells of ½-area plates (Corning, cat. no. 3688) were filled with this cell suspension at 50 µl/well or with 50 µl PBS (Invitrogen, cat. no. 10010). Assay plates were incubated overnight at 37° C., 5% $CO_2$ and 95% Relative Humidity.

On the second day, 2× concentrated Assay Buffer was prepared: 4% FBS (Sigma, cat. no. F2442) in RPMI 1640 (Promega kit or Life Technologies, cat. no. 21875) at room temperature. 2× concentrated test and control IgG solutions were prepared in PBS. Serial dilutions of test and control IgG's were also made in PBS in U-bottom plates (Nunc, cat. no. 268152), starting with 10 µg/ml and performing 6-step 4-fold titration. Positive and negative control IgG serial dilutions were prepared in PBS on separate deep well plates (Greiner Bio-one, cat. no. 780270). Basal control, which is control without IgG was also prepared. IgG's of which activities need to be compared directly were incubated on same plate as much as possible, to avoid inter-plate variation.

Assay plates were taken out of the incubator and flicked to empty wells. 20 µl of IgG solution was added to assay plate, starting with transfer of lowest IgG concentration followed by higher concentration with same pipet tips.

Required number of PD-1 effector cells (J115A: 1 vial per 32 IgG's to be tested) were removed from freezer, thawed quickly at 37° C. and gently mixed by pipetting up and down, Cells from all vials were transferred to a 50 ml tube. 2× concentrated Assay Buffer (5.9 ml per vial of cells) was slowly added to cells such that volume doubled per minute. 20 µl of effector cell suspension was added to wells on assay plates. Plates were incubated for 6 hours at 37° C., 5% CO2 and 95% Relative Humidity. Following 6 hours incubation, plates were pre-incubated at room temperature for 10 min.

Luciferase activity was measured using the Bio-Glo™ luciferase Assay System (Promega, cat. no. G7941). Bio-Glo™ Luciferase Assay Buffer (protected from light) was equilibrated to room temperature overnight and thoroughly mixed with Bio-Glo™ Luciferase Assay Substrate. 40 µl of Bio-Glo luciferase was added to each well on the assay plate and luminescence measured after 5-10 min on EnVision plate reader (PerkinElmer, Model 2104-0040A Luminescence mode). Readout was obtained in Relative light unit (RLU) values. Fold Induction which is ratio of experimental activity to control activity was calculated as RLU value of IgG-X/RLU value of no IgG. Fold Induction was plotted against log IgG concentrations and the sigmoid curve fitted in GraphPad Prism using nonlinear regression and the log(inhibitor) vs. response (three parameters) equation.

Results are shown in FIG. 1. All controls displayed the expected activities and were consistent in different plates. The affinity matured variants were at least as potent as their parental IgG, and as potent or more potent than nivolumab analog 1. EC50 values of the affinity matured variants and parental antibodies are shown in Table 1.

TABLE 1

EC50 values of affinity matured variants and parental antibodies.

| IgG comprising a VH having amino acid sequence: | EC50 (nM) | EC50 (nM) nivolumab analog |
|---|---|---|
| SEQ ID NO: 1 | 3.81 | 3.47 |
| SEQ ID NO: 2 | 4.49 | |
| SEQ ID NO: 6 | 2.87 | |
| SEQ ID NO: 9 | 5.65 | |
| SEQ ID NO: 5 | 4.91 | 5.79 |
| SEQ ID NO: 4 | 4.12 | |
| SEQ ID NO: 3 | 4.20 | |
| SEQ ID NO: 10 | 11.05 | |

Example 3—Binding Characteristics

The binding affinity of selected affinity matured PD-1 binding domains was determined using SPR. The binding affinity for human PD-1 was determined in bivalent monospecific IgG format and compared with the binding affinity of bivalent monospecific analogs of reference antibody nivolumab and a bivalent bispecific antibody comprising a binding domain having the sequence of reference antibody nivolumab and a binding domain that binds an unrelated target.

SPR experiments were performed using a Biacore 8K instrument (GE Healthcare) at 25° C. The SPR running buffer (10 mM HEPES, 150 mM NaCl, 3 mM EDTA and 0.05% v/v Surfactant P20, pH 7.4) was prepared from 10×HBS-EP Buffer (GE Healthcare). Anti-human Fc antibodies (GE Healthcare) were immobilized via amine coupling on all sixteen flow cells of an S series sensor chip CM5 (GE Healthcare). The immobilization levels are ~9000 RU for all flow cells. The desired capturing level (100-150 RU) of anti-PD-1 antibodies was achieved by flowing appropriate concentration of anti-PD-1 antibodies through the active flow cell of each channel for 60 seconds with 10 µL/min flow rate. Then, a PD-1 three-fold serial dilution concentration series (total 7 concentrations, highest at 300 nM) prepared from PD-1 stock (R&D 8986-PD) and running buffer (0 concentration) were injected for 240 seconds (association time) immediately followed by running buffer for 480 seconds (dissociation time) at a flow rate of 45 Surface was regenerated with 30-second injection of 3 M $MgCl_2$ with 30 µL/min flow rate. Binding kinetics and affinity parameters were obtained from a global fit of the data to 1 to 1 binding model.

Data is shown in FIG. 2. IgG's comprising the PD-1 binding domains of the present disclosure have an at least ten-fold higher binding affinity ($K_D$) than the analogs of the reference antibody.

Binding affinity was also determined in bispecific IgG format using SPR on a BIAcore-T200 instrument using an anti-huIgG antibody immobilized on a CM5 Series S sensor chip. It was also assessed if the two human proteins can be engaged simultaneously by the bispecific antibodies. The binding affinity of bispecific antibodies comprising a PD-1 binding domain comprising a heavy chain variable region having SEQ ID NO: 7 or a PD-1 binding domain comprising a heavy chain variable region having SEQ ID NO: 8 to human PD-1 and cynomolgus PD-1 was determined. The antibody format used is PD-1×Antigen A, wherein Antigen A is an arbitrarily selected antigen not reactive with PD-1 and not impacting PD-1 binding tested in the assay. Each binding domain of the bispecific antibodies comprises a heavy chain and a light chain. The binding affinity of the bispecific antibodies was compared with the binding affinity of an analog of reference antibody nivolumab, which comprises two anti-PD-1 binding domains.

Reference antibodies used were: nivolumab analog (SEQ ID NO: 13/SEQ ID NO: 14) and a reference antibody against antigen A. An antibody against an unrelated target was used as a negative control for binding. Test antibodies were SEQ ID NO: 7× Antigen A and SEQ ID NO: 8× Antigen A.

Monomeric recombinant antigens used were: hu-Antigen A, cy-Antigen A, huPD-1 (huPD-1-His, Sino Biological, cat. nr. 10377-H08H) and cyPD-1 (cyPD-1-His, R&D Systems, cat. nr. 8509-PD).

Immobilization

Immobilization of goat anti-huIgG Fc (JIR, cat. nr. 109-005-098) on four flow channels of a CM5 sensor chip (GE Healthcare; Cat. Nr. BR-1005-30) was performed by amine coupling, using 40 µg/ml of the antibody diluted in 10 mM acetate pH 5.0. The following conditions were used: activation time of 420 seconds, deactivation time of 420 seconds, deactivation buffer: 1 M ethanolamine pH 8.5. A high density of immobilization was achieved, ranging from 9158 to 9428 RU.

Affinity Determination

Fax affinity determination, test and control antibodies were captured by anti-huIgG antibody immobilized on the CM5 sensor chip at a flow rate of 30 µl/min for 60 seconds in only one flow cell. Captured antibody concentration was 20 nM for PD-1 affinity determination and 10 nM for Antigen A affinity determination. This was followed by a stabilization period of 60 seconds with buffer at a flow rate of 30 µl/min. Five step, two fold, serial dilutions of the antigens were injected, at 30 µl/min, for 60 seconds, in both the flow cell with the captured antibody and a reference flow cell (no captured antibody). Antigen concentrations were 80 nM down to 2.5 nM for huPD-1 and cyPD-1, and 40 to 1.25 nM for hu-Antigen A and cy-Antigen A. Background correction for buffer effects was performed by injection with buffer alone and the reference flow cell was used for background subtraction.

Following antibody—antigen interaction, an off-rate wash of 300 seconds, at 30 µl/min was done. Regeneration between cycles was done using two 15 µl injections of 10 mM Glycine pH 1.5 at 30 µl/min, followed by a stabilization step of 90 seconds at 90 µl/min. To confirm total regeneration and assay consistency, a repeat run of the reference antibody with all the tested antigen concentrations was performed at the end of the assay and for all antigens tested.

HBS-EP+ buffer was used for PD-1 affinity determination, while, for Antigen A, HBS-EP+ was supplemented with NaCl to a final concentration of 500 nM NaCl, in order to avoid unspecific binding.

Results were analyzed in Biacore T200 Evaluation Software. The raw RU signal were blank subtracted (channel with no captured antibody) and background corrected for buffer effects (subtraction of the run with captured antibody but with buffer in the second injection, instead of antigen). 1:1 binding Langmuir fitting was applied to the set of sample curves, using the simultaneous fitting option of the Biacore T200 Evaluation Software to calculate association rate (ka), dissociation rate (kd) and affinity (KD).

The captured bispecific and reference antibodies showed binding to the respective recombinant antigens. No binding of the antigen to the negative control antibody was observed.

An overview of the data is provided in FIG. 3. For huPD-1, the two bispecific antibodies had similar affinity, both showing more than 10 fold improvement in KD over the reference antibody nivolumab analog, mainly due to the slower dissociation observed. For cyPD-1-His, SEQ ID NO: 7×Antigen A showed approximately 10 fold improvement over nivolumab analog mainly due to the slower dissociation.

Simultaneous Binding

Simultaneous binding of the bispecific antibodies to hu-Antigen A and huPD-1 was assayed with a similar set-up as for affinity determination. An immobilized anti-huIgG was used to capture the bispecific antibodies. A mix of nivolumab analog and Antigen A reference antibody was included as a positive control and an antibody against an unrelated target was included as negative control. Then, one of the antigens was injected at a saturating concentration (80 nM for huPD-1 and 40 nM for hu-Antigen A) for 300 sec, to occupy all antigen binding sites. The second antigen was injected sequentially at the same concentration used in injection 1, either alone or in combination with the first antigen (to ensure that all binding sites remained occupied). High salt buffer was used during the whole process, to prevent hu-Antigen A unspecific binding.

| SEQUENCES |
|---|

SEQ ID NO: 1 - Heavy chain variable region - CDRs indicated in bold and underlined according to Kabat
QVQLQESGPGLVKPSETLSLTCTVSNGSLGFDFWSWIRQPPGRGLEWIGYIYYSGSW SLNPSFKGRVTMSVDTSKNQFSLNLRSVTAADTAVYYCARGGYTGYGGDWFDPW GQGTLVTVSS SEQ ID NO: 2- Heavy chain variable region - CDRs indicated in bold and underlined according to Kabat
QVQLQESGPGLVKPSETLSLTCTVSNGSLGFEFWSWIRQPPGRGLEWIGYIVYSGSH SVSPSLKTRVTMSVDTSKNQFSLNLRSVTAADTAVYYCARGGYTGHGGDWFDTW GQGTLVTVSS SEQ ID NO: 3- Heavy chain variable region - CDRs indicated in bold and underlined according to Kabat
QVQLVQSGSELKKPGASVKVSCKASGYTFTRFALSWVRQAPGQGLEWMGWIDPNT GTPTYAQDFTGRFVFSLDTSVTTAYLQISSLKAEDTAVYYCARSLGYCGSDICYPN GILDNWGQGTLVTVSS SEQ ID NO: 4- Heavy chain variable region - CDRs indicated in bold and underlined according to Kabat
QVQLVQSGSELKKPGASVKVSCKASGYTFTRFAVNWVRQAPGQGLEWMGWIDPN TGTPTYAQGVTNRFVFSLDTSVTTAYLQISSLKAEDTAVYYCARSLGYCSSDICYP NLIFDNWGQGTLVTVSS SEQ ID NO: 5 - Heavy chain variable region - CDRs indicated in bold and underlined according to Kabat
QVQLVQSGSELKKPGASVKVSCKASGYTFTRFALHWVRQAPGQGLEWMGWIDPN TGTPTFAQGVTGRFVFSLDTSVTTAYLQISSLKAEDTAVYYCARSLGYCDSDICYP NWIFDNWGQGTLVTVSS SEQ ID NO: 6- Heavy chain variable region - CDRs indicated in bold and underlined according to Kabat
QVQLQESGPGLVKPSETLSLTCTVSDGSIGYHFWSWIRQPPGRGLEWIGYIVYSGSY NVNPSLKTRVTMSVDTSKNQFSLNLRSVTAADTAVYYCARGGYTGYGGDWFDP WGQGTLVTVSS SEQ ID NO: 7- Heavy chain variable region - CDRs indicated in bold and underlined according to Kabat
QVQLQESGPGLVKPSETLSLTCTVSEGSIGYHFWSWIRQPPGRGLEWIGYIVYSGSY NVNPSLKTRVTMS VDTSKNQFSLNLRSVTAADTAVYYCARGGYTGYGGDWFDPWGQGTLVTVSS SEQ ID NO: 8- Heavy chain variable region - CDRs indicated in bold and underlined according to Kabat
QVQLVQSGSELKKPGASVKVSCKASGYTFTRFALHWVRQAPGQGLEWMGWIDPN TGTPTFAQGVTGRFVFSLDTSVTTAYLQISSLKAEDTAVYYCARSLGYCDSDICYP NWIFDNWGQGTLVTVSS SEQ ID NO: 9- Heavy chain variable region - CDRs indicated in bold and underlined according to Kabat
QVQLQESGPGLVKPSETLSLTCTVSNGSLGFYFWSWIRQPPGRGLEWIGYIYYSGST SFNPSLKSRVTMSVDTSKNQFSLNLRSVTAADTAVYYCARGGYTGYGGDWFDPW GQGTLVTVSS SEQ ID NO: 10 - Heavy chain variable region - CDRs indicated in bold and underlined according to Kabat
QVQLVQSGSELKKPGASVKVSCKASGYTFTRFTMSWVRQAPGQGLEWMGWINPN TGNPTYAQDFTGRFVFSLDTSVTTAYLQISSLKAEDTAVYYCARILGYCNTDNCYP NWIFDYWGQGTLVTVSS SEQ ID NO: 11 - Heavy chain nivolumab analog 1
QVQLVESGGGVVQPGRSLRLDCKASGITFSNSGMHWVRQAPGKGLEWVAVIWYDG
SKRYYADSVKGRFTISRDNSKNTLFLQMNSLRAEDTAVYYCATNDDYWGQGTLVT
VSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCDKTHTCPPCP
APELGRGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK SEQ ID NO: 12 - Heavy chain nivolumab analog 2
QVQLVESGGGVVQPGRSLRLDCKASGITFSNSGMHWVRQAPGKGLEWVAVIWYDG
SKRYYADSVKGRFTISRDNSKNTLFLQMNSLRAEDTAVYYCATNDDYWGQGTLVT
VSSASTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCPAPE
FLGGPSVFLFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTPPVLDSDGS
FFLYSRLTVDKSRWQEGNVFSCSVMHEALHNHYTQKSLSLSLGK

SEQUENCES

SEQ ID NO: 13 - Heavy chain nivolumab analog 4
QVQLVESGGGVVQPGRSLRLDCKASGITFSNSGMHWVRQAPGKGLEWVAVIWYDG
SKRYYADSVKGRFTISRDNSKNTLFLQMNSLRAEDTAVYYCATNDDYWGQGTLVT
VSSASTKGPSVFPLAPCSRSTSESTAALGCLVKDYFPEPVTVSWNSGALTSGVHTFPA
VLQSSGLYSLSSVVTVPSSSLGTKTYTCNVDHKPSNTKVDKRVESKYGPPCPPCPAPE
FLGGPSVFLFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTISKAKGQPREP
QVYTLPPSQEEMTKNQVSLTCLVKGFYPSDIAVEWESNGQPENNYKTTPPVLDSDGS
FFLYSRLWDKSRWQEGNVFSCSVMHEALHNHYTQKSLSLSLGK SEQ ID NO: 14 - Light chain nivolumab
EIVLTQSPATLSLSPGERATLSCRASQSVSSYLAWYQQKPGQAPRLLIYDASNRATGI
PARFSGSGSGTDFTLTISSLEPEDFAVYYCQQSSNWPRTFGQGTKVEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 15 - Heavy chain variable region
EVQLVESGGGVVQPGRSLRLSCAASGFTFSNYGMHWVRQAPGKGLEWVAVISYDG
STKYSADSLKGRFTISRDNSKNTLYLQMNSLRADDTAVYYCAKEGWSFDSSGYRSW
FDSWGQGTLVT SEQ ID NO: 16 - Light chain variable region - CDRs indicated in bold and underlined
according to IMGT
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPPTFGQGTKVEIK SEQ ID NO: 17-CH1 WT
ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKRV SEQ ID NO: 18 - CH2
APELLGGPSVFLFPPKPKDTLMISRTPEVTCVVVDVSHEDPEVKFNWYVDGVEVHNA
KTKPREEQYASTYRVVSVLTVLHQDWLNGKEYKCKVSNKALPAPIEKTISKAK SEQ ID NO: 19 - CH3
GQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK SEQ ID NO: 20 - Nivolumab analog heavy chain variable region
QVQLVESGGGVVQPGRSLRLDCKASGITFSNSGMHWVRQAPGKGLEWVAVIWYDG
SKRYYADSVKGRFTISRDNSKNTLFLQMNSLRAEDTAVYYCATNDDYWGQGTLVT
VSS SEQ ID NO: 21 - Nivolumab analog light chain variable region
EIVLTQSPATLSLSPGERATLSCRASQSVSSYLAWYQQKPGQAPRLLIYDASNRATGI
PARFSGSGSGTDFTLTISSLEPEDFAVYYCQQSSNWPRTFGQGTKVEIK SEQ ID NO: 22 - HCDR1 according to Kabat
FYFWS SEQ ID NO: 23 - HCDR2 according to Kabat
YIYYSGSTSFNPSLKS SEQ ID NO: 24 - HCDR3 according to Kabat
GGYTGYGGDWFDP SEQ ID NO: 25 - HCDR1 according to Kabat
FDFWS SEQ ID NO: 26 - HCDR2 according to Kabat
YIYYSGSWSLNPSFKG SEQ ID NO: 27 - HCDR3 according to Kabat
GGYTGYGGDWFDP SEQ ID NO: 28 - HCDRI according to Kabat
FEFWS SEQ ID NO: 29 - HCDR2 according to Kabat
YIVYSGSHSVSPSLKT SEQ ID NO: 30 - HCDR3 according to Kabat
GGYTGHGGDWFDT SEQ ID NO: 31 - HCDR1 according to Kabat
RFALS

| SEQUENCES |
|---|

SEQ ID NO: 32 - HCDR2 according to Kabat
WIDPNTGTPTYAQDFTG

SEQ ID NO: 33 - HCDR3 according to Kabat
SLGYCGSDICYPNGILDN

SEQ ID NO: 34 - HCDR1 according to Rabat
RFAVN

SEQ ID NO: 35 - HCDR2 according to Kabat
WIDPNTGTPTYAQGVTN

SEQ ID NO: 36 - HCDR3 according to Kabat
SLGYCSSDICYPNLIFDN

SEQ ID NO: 37 - HCDRI according to Kabat
RFALH

SEQ ID NO: 38 - HCDR2 according to Kabat
WIDPNTGTPTFAQGVTG

SEQ ID NO: 39 - HCDR3 according to Kabat
SLGYCDSDICYPNWIFDN

SEQ ID NO: 40 - HCDR1 according to Kabat
YHFWS

SEQ ID NO: 41 - HCDR2 according to Kabat
YIVYSGSYNVNPSLKT

SEQ ID NO: 42 - HCDR3 according to Kabat
GGYTGYGGDWFDP

SEQ ID NO: 43 - HCDR1 according to Kabat
YHFWS

SEQ ID NO: 44 - HCDR2 according to Kabat
YIVYSGSYNVNPSLKT

SEQ ID NO: 45 - HCDR3 according to Kabat
GGYTGYGGDWFDP

SEQ ID NO: 46 - HCDR1 according to Kabat
RFALH

SEQ ID NO: 47 - HCDR2 according to Kabat.
WIDPNTGTPTFAQGVTG

SEQ ID NO: 48 - HCDR3 according to Kabat
SLGYCDSDICYPNWIFDN

SEQ ID NO: 49 LCDR1 according to IMGT
QSISSY

SEQ ID NO: 50 LCDR2 according to IMGT
AAS

SEQ ID NO: 51 LCDR3 according to IMGT
QQSYSTPPT

SEQ ID NO: 52 Light chain variable region - CDRs indicated in bold and underlined according to IMGT
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPPITFGQGTRLEIK SEQ ID NO: 53 Light chain variable region - CDRs indicated in bold and underlined according to IMGT
EIVMTQSPATLSVSPGERATLSCRASQSVSSNLAWYQQKPGQAPRLLIYGASTRATGI
PARFSGSGSGTEFTLTISSLQSEDFAVYYCQQYNNWPWTFGQGTKVEIK SEQ ID NO: 54 Light chain variable region - CDRs indicated in bold and underlined according to IMGT
EIVLTQSPGTLSLSPGERATLSCRASQSVSSSYLAWYQQKPGQAPRLLIYGASSRATGI
PDRFSGSGSGTDFTLTISRLEPEDFAVYYCQQYGSSPWTFGQGTKVEIK

| SEQUENCES |
| --- |
| SEQ ID NO: 55 Light chain variable region - CDRs indicated in bold and underlined according to IMGT<br>SYVLTQPPSVSVAPGETARITCGGDNIGRKSVYWYQQKSGQAPVLVIYYDSDRPSGI<br>PERFSGSNSGNTATLTISRVEAGDEADYYCQVWDGSSDHWVFGGGTKLTVL<br><br>SEQ ID NO: 56 V region<br>DIQMTQSPSSLSASVGDRVTITCRASQSISSYLNWYQQKPGKAPKLLIYAASSLQSGV<br>PSRFSGSGSGTDFTLTISSLQPEDFATYYCQQSYSTP<br><br>SEQ ID NO: 57 V region<br>EIVMTQSPATLSVSPGERATLSCRASQSVSSNLAWYQQKPGQAPRLLIYGASTRATGI<br>PARFSGSGSGTEFTLTISSLQSEDFAVYYCQQYNNWP<br><br>SEQ ID NO: 58 V region<br>EIVLTQSPGTLSLSPGERATLSCRASQSVSSSYLAWYQQKPGQAPRLLIYGASSRATGI<br>PDRFSGSGSGTDFTLTISRLEPEDFAVYYCQQYGSSP<br><br>SEQ ID NO: 59 V region<br>SYVLTQPPSVSVAPGETARITCGGDNIGRKSVYWYQQKSGQAPVLVIYYDSDRPSGIP<br>ERFSGSNSGNTATLTISRVEAGDEADYYCQVWDGSSDH<br><br>SEQ ID NO: 60 Light chain constant region<br>RTVAAPSVFIFPPSDEQLKSGTASVVCLLNNFYPREAKVQWKVDNALQSGNSQESVT<br>EQDSKDSTYSLSSTLTLSKADYEKHKVYACEVTHQGLSSPVTKSFNRGEC |

The invention claimed is:

1. An anti-human PD-1 binding domain comprising a heavy chain variable region, wherein the heavy chain variable region comprises:
   a) heavy chain CDR1 (HCDR1), heavy chain CDR2 (HCDR2), and heavy chain CDR3 (HCDR3), having an amino acid sequence as set forth in SEQ ID NO: 22, SEQ ID NO: 23 and SEQ ID NO: 24, respectively;
   b) heavy chain CDR1 (HCDR1), heavy chain CDR2 (HCDR2), and heavy chain CDR3 (HCDR3), having an amino acid sequence as set forth in SEQ ID NO: 25, SEQ ID NO: 26, and SEQ ID NO: 27, respectively;
   c) heavy chain CDR1 (HCDR1), heavy chain CDR2 (HCDR2), and heavy chain CDR3 (HCDR3), having an amino acid sequence as set forth in SEQ ID NO: 28, SEQ ID NO: 29, and SEQ ID NO: 30, respectively;
   d) heavy chain CDR1 (HCDR1), heavy chain CDR2 (HCDR2), and heavy chain CDR3 (HCDR3), having an amino acid sequence as set forth in SEQ ID NO: 31, SEQ ID NO: 32, and SEQ ID NO: 33, respectively;
   e) heavy chain CDR1 (HCDR1), heavy chain CDR2 (HCDR2), and heavy chain CDR3 (HCDR3), having an amino acid sequence as set forth in SEQ ID NO: 34, SEQ ID NO: 35, and SEQ ID NO: 36, respectively;
   f) heavy chain CDR1 (HCDR1), heavy chain CDR2 (HCDR2), and heavy chain CDR3 (HCDR3), having an amino acid sequence as set forth in SEQ ID NO: 37, SEQ ID NO: 38, and SEQ ID NO: 39, respectively;
   g) heavy chain CDR1 (HCDR1), heavy chain CDR2 (HCDR2), and heavy chain CDR3 (HCDR3), having an amino acid sequence as set forth in SEQ ID NO: 40, SEQ ID NO: 41, and SEQ ID NO: 42, respectively;
   h) heavy chain CDR1 (HCDR1), heavy chain CDR2 (HCDR2), and heavy chain CDR3 (HCDR3), having an amino acid sequence as set forth in SEQ ID NO: 43, SEQ ID NO: 44, and SEQ ID NO: 45, respectively; or
   i) heavy chain CDR1 (HCDR1), heavy chain CDR2 (HCDR2), and heavy chain CDR3 (HCDR3), having an amino acid sequence as set forth in SEQ ID NO: 46, SEQ ID NO: 47, and SEQ ID NO: 48, respectively.

2. The anti-human PD-1 binding domain according to claim 1, comprising a heavy chain variable region having an amino acid sequence as set forth in any one of SEQ ID NO: 1-9 or having at least 90% sequence identity thereto.

3. The anti-human PD-1 binding domain according to claim 1, comprising a heavy chain variable region having an amino acid sequence as set forth in any one of SEQ ID NO: 1-9.

4. The anti-human PD-1 binding domain according to claim 1, further comprising a light chain variable region, wherein the light chain variable region comprises a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

5. The anti-human PD-1 binding domain according to claim 2, further comprising a light chain variable region having an amino acid sequence as set forth in SEQ ID NO: 16, or having at least 90% sequence identity thereto.

6. The anti-human PD-1 binding domain according to claim 4, wherein the light chain variable region comprises an amino acid sequence as set forth in SEQ ID NO: 16, or having at least 90% sequence identity thereto.

7. The anti-human PD-1 binding domain according to claim 3, further comprising a light chain variable region having an amino acid sequence as set forth in SEQ ID NO: 16.

8. The anti-human PD-1 binding domain according to claim 4, further comprising a CH1 and CL region.

9. The anti-human PD-1 binding domain according to claim 1, wherein the heavy chain variable region comprises:
   a heavy chain CDR1 (HCDR1), heavy chain CDR2 (HCDR2), and heavy chain CDR3 (HCDR3), having an amino acid sequence as set forth in SEQ ID NO: 22, SEQ ID NO: 23 and SEQ ID NO: 24, respectively;

and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

10. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 25, SEQ ID NO: 26, and SEQ ID NO: 27, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

11. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 28, SEQ ID NO: 29, and SEQ ID NO: 30, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

12. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 31, SEQ ID NO: 32, and SEQ ID NO: 33, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

13. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 34, SEQ ID NO: 35, and SEQ ID NO: 36, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

14. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 37, SEQ ID NO: 38, and SEQ ID NO: 39, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

15. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 40, SEQ ID NO: 41, and SEQ ID NO: 42, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

16. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 43, SEQ ID NO: 44, and SEQ ID NO: 45, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

17. The anti-human PD-1 binding domain according to claim 1, wherein the heavy chain variable region comprises:
a heavy chain CDR1 (HCDR1), heavy chain CDR2 (HCDR2), and heavy chain CDR3 (HCDR3), having an amino acid sequence as set forth in SEQ ID NO: 46, SEQ ID NO: 47, and SEQ ID NO: 48, respectively;
and further comprising a light chain variable region comprising a light chain CDR1 (LCDR1), light chain CDR2 (LCDR2), and light chain CDR3 (LCDR3), having an amino acid sequence as set forth in SEQ ID NO: 49, SEQ ID NO: 50, and SEQ ID NO: 51, respectively.

18. A binding moiety, wherein the binding moiety comprises an anti-PD-1 binding domain as claimed in claim 4.

19. The binding moiety according to claim 18, wherein the binding moiety is a monospecific binding moiety.

20. A pharmaceutical composition comprising an effective amount of an anti-human PD-1 binding domain according to claim 4, and a pharmaceutically acceptable carrier.

* * * * *

SEQUENCE LISTING

<160> NUMBER OF SEQ ID NOS: 66

<210> SEQ ID NO 1
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Asn Gly Ser Leu Gly Phe Asp
            20                  25                  30

Phe Trp Ser Trp Ile Arg Gln Pro Pro Gly Arg Gly Leu Glu Trp Ile
        35                  40                  45

Gly Tyr Ile Tyr Tyr Ser Gly Ser Trp Ser Leu Asn Pro Ser Phe Lys
    50                  55                  60

Gly Arg Val Thr Met Ser Val Asp Thr Ser Lys Asn Gln Phe Ser Leu
65                  70                  75                  80

Asn Leu Arg Ser Val Thr Ala Ala Asp Thr Ala Val Tyr Tyr Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 2

```
Gln Val Gln Leu Gln Glu Ser Gly Pro Gly Leu Val Lys Pro Ser Glu
1               5                   10                  15

Thr Leu Ser Leu Thr Cys Thr Val Ser Asn Gly Ser Leu Gly Phe Glu
            20                  25                  30

Phe Trp Ser Trp Ile Arg Gln Pro Pro Gly Arg Gly Leu Glu Trp Ile
        35                  40                  45

Gly Tyr Ile Val Tyr Ser Gly Ser His Ser Val Ser Pro Ser Leu Lys
    50                  55                  60

Thr Arg Val Thr Met Ser Val Asp Thr Ser Lys Asn Gln Phe Ser Leu
65                  70                  75                  80

Asn Leu Arg Ser Val Thr Ala Ala Asp Thr Ala Val Tyr Tyr Cys Ala
                85                  90                  95

Arg Gly Gly Tyr Thr Gly His Gly Gly Asp Trp Phe Asp Thr Trp Gly
            100                 105                 110

Gln Gly Thr Leu Val Thr Val Ser Ser
            115                 120
```

<210> SEQ ID NO 3
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 3

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Phe
            20                  25                  30

Ala Leu Ser Trp Val Arg Gln Ala Pro Gly Gln Gly Leu Glu Trp Met
        35                  40                  45

Gly Trp Ile Asp Pro Asn Thr Gly Thr Pro Thr Tyr Ala Gln Asp Phe
    50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Leu Gly Tyr Cys Gly Ser Asp Ile Cys Tyr Pro Asn Gly
            100                 105                 110

Ile Leu Asp Asn Trp Gly Gln Gly Thr Leu Val Thr Val Ser Ser
        115                 120                 125
```

<210> SEQ ID NO 4
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 4

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Phe
            20                  25                  30

Ala Val Asn Trp Val Arg Gln Ala Pro Gly Gln Gly Leu Glu Trp Met
        35                  40                  45

Gly Trp Ile Asp Pro Asn Thr Gly Thr Pro Thr Tyr Ala Gln Gly Val
    50                  55                  60
```

Thr Asn Arg Phe Val Phe Ser Leu Asp Thr Ser Val Thr Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Ser Leu Gly Tyr Cys Ser Ser Asp Ile Cys Tyr Pro Asn Leu
            100                 105                 110

Ile Phe Asp Asn Trp Gly Gln Gly Thr Leu Val Thr Val Ser Ser
        115                 120                 125

<210> SEQ ID NO 5
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Phe
            20                  25                  30

Ala Leu His Trp Val Arg Gln Ala Pro Gly Gln Gly Leu Glu Trp Met
        35                  40                  45

Gly Trp Ile Asp Pro Asn Thr Gly Thr Pro Thr Phe Ala Gln Gly Val
    50                  55                  60

Thr Gly Arg Phe Val Phe Ser Leu Asp Thr Ser Val Thr Thr Ala Tyr
 65                 70                  75                  80

Leu Gln Ile Ser Ser Leu Lys Ala Glu Asp Thr Ala Val Tyr Tyr Cys
                85                  90                  95

Ala Arg Ser Leu Gly Tyr Cys Ser Ser Asp Ile Cys Tyr Pro Asn Trp
            100                 105                 110

Ile Phe Asp Asn Trp Gly Gln Gly Thr Leu Val Thr Val Ser Ser
        115                 120                 125

<210> SEQ ID NO 6
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Asp Gly Ser Ile Gly Tyr His
            20                  25                  30

Phe Trp Ser Trp Ile Arg Gln Pro Pro Gly Arg Gly Leu Glu Trp Ile
        35                  40                  45

Gly Tyr Ile Val Tyr Ser Gly Ser Tyr Asn Val Asn Pro Ser Leu Lys
    50                  55                  60

Thr Arg Val Thr Met Ser Val Asp Thr Ser Lys Asn Gln Phe Ser Leu
 65                 70                  75                  80

Asn Leu Arg Ser Val Thr Ala Ala Asp Thr Ala Val Tyr Tyr Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser

-continued

```
            115                 120

<210> SEQ ID NO 7
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Glu Gly Ser Ile Gly Tyr His
            20                  25                  30

Phe Trp Ser Trp Ile Arg Gln Pro Pro Gly Arg Gly Leu Glu Trp Ile
        35                  40                  45

Gly Tyr Ile Val Tyr Ser Gly Ser Tyr Asn Val Asn Pro Ser Leu Lys
    50                  55                  60

Thr Arg Val Thr Met Ser Val Asp Thr Ser Lys Asn Gln Phe Ser Leu
65                  70                  75                  80

Asn Leu Arg Ser Val Thr Ala Ala Asp Thr Ala Val Tyr Tyr Cys Ala
                85                  90                  95

Arg Gly Gly Tyr Thr Gly Tyr Gly Gly Asp Trp Phe Asp Pro Trp Gly
            100                 105                 110

Gln Gly Thr Leu Val Thr Val Ser Ser
        115                 120

<210> SEQ ID NO 8
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 8

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Phe
            20                  25                  30

Ala Leu His Trp Val Arg Gln Ala Pro Gly Gln Gly Leu Glu Trp Met
        35                  40                  45

Gly Trp Ile Asp Pro Asn Thr Gly Thr Pro Thr Phe Ala Gln Gly Val
    50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Leu Gly Tyr Cys Asp Ser Asp Ile Cys Tyr Pro Asn Trp
            100                 105                 110

Ile Phe Asp Asn Trp Gly Gln Gly Thr Leu Val Thr Val Ser Ser
        115                 120                 125

<210> SEQ ID NO 9
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 9
```

```
Gln Val Gln Leu Gln Glu Ser Gly Pro Gly Leu Val Lys Pro Ser Glu
1               5                   10                  15

Thr Leu Ser Leu Thr Cys Thr Val Ser Asn Gly Ser Leu Gly Phe Tyr
            20                  25                  30

Phe Trp Ser Trp Ile Arg Gln Pro Pro Gly Arg Gly Leu Glu Trp Ile
            35                  40                  45

Gly Tyr Ile Tyr Tyr Ser Gly Ser Thr Ser Phe Asn Pro Ser Leu Lys
50                      55                  60

Ser Arg Val Thr Met Ser Val Asp Thr Ser Lys Asn Gln Phe Ser Leu
65                  70                  75                  80

Asn Leu Arg Ser Val Thr Ala Ala Asp Thr Ala Val Tyr Tyr Cys Ala
                85                  90                  95

Arg Gly Gly Tyr Thr Gly Tyr Gly Gly Asp Trp Phe Asp Pro Trp Gly
                100                 105                 110

Gln Gly Thr Leu Val Thr Val Ser Ser
            115                 120

<210> SEQ ID NO 10
<211> LENGTH: 127
<212> TYPE: PRT
<213> ORGANISM: Artificial Sequence
<220> FEATURE:
<223> OTHER INFORMATION: Heavy chain variable region

<400> SEQUENCE: 10

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Arg Phe
            20                  25                  30

Thr Met Ser Trp Val Arg Gln Ala Pro Gly Gln Gly Leu Glu Trp Met
            35                  40                  45

Gly Trp Ile Asn Pro Asn Thr Gly Asn Pro Thr Tyr Ala Gln Asp Phe
50                      55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Leu Gly Tyr Cys Asn Thr Asp Asn Cys Tyr Pro Asn Trp
                100                 105                 110

Ile Phe Asp Tyr Trp Gly Gln Gly Thr Leu Val Thr Val Ser Ser
            115                 120                 125

<210> SEQ ID NO 11
<211> LENGTH: 443
<212> TYPE: PRT
<213> ORGANISM: Artificial Sequence
<220> FEATURE:
<223> OTHER INFORMATION: Heavy chain Nivolumab analog 1

<400> SEQUENCE: 11

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
```

```
            50                  55                  60
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Gly Arg Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 12
<211> LENGTH: 440
<212> TYPE: PRT
<213> ORGANISM: Artificial Sequence
```

<220> FEATURE:
<223> OTHER INFORMATION: Heavy chain Nivolumab analog 2

<400> SEQUENCE: 12

```
Gln Val Gln Leu Val Glu Ser Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

```
Ser Arg Leu Thr Val Asp Lys Ser Arg Trp Gln Glu Gly Asn Val Phe
            405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 13
<211> LENGTH: 440
<212> TYPE: PRT
<213> ORGANISM: Artificial Sequence
<220> FEATURE:
<223> OTHER INFORMATION: Heavy chain Nivolumab analog 4

<400> SEQUENCE: 13

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320
```

```
Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 14
<211> LENGTH: 214
<212> TYPE: PRT
<213> ORGANISM: Artificial Sequence
<220> FEATURE:
<223> OTHER INFORMATION: Light chain Nivolumab

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 15
```

```
<211> LENGTH: 122
<212> TYPE: PRT
<213> ORGANISM: Artificial Sequence
<220> FEATURE:
<223> OTHER INFORMATION: Heavy chain variable region

<400> SEQUENCE: 15

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Thr Lys Tyr Ser Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Lys Glu Gly Trp Ser Phe Asp Ser Ser Gly Tyr Arg Ser Trp Phe
            100                 105                 110

Asp Ser Trp Gly Gln Gly Thr Leu Val Thr
        115                 120

<210> SEQ ID NO 16
<211> LENGTH: 107
<212> TYPE: PRT
<213> ORGANISM: Artificial Sequence
<220> FEATURE:
<223> OTHER INFORMATION: Light chain variable region

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys
            100                 105

<210> SEQ ID NO 17
<211> LENGTH: 98
<212> TYPE: PRT
<213> ORGANISM: Artificial Sequence
<220> FEATURE:
<223> OTHER INFORMATION: CH1 WT

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val

<210> SEQ ID NO 18
<211> LENGTH: 110
<212> TYPE: PRT
<213> ORGANISM: Artificial Sequence
<220> FEATURE:
<223> OTHER INFORMATION: CH2

<400> SEQUENCE: 18

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
     50                  55                  60

Gln Tyr Ala Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 19
<211> LENGTH: 107
<212> TYPE: PRT
<213> ORGANISM: Artificial Sequence
<220> FEATURE:
<223> OTHER INFORMATION: CH3

<400> SEQUENCE: 19

Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
             20                  25                  30

Tyr Pro Ser Asp Ile Ala Val Glu Trp Glu Ser Asn Gly Gln Pro Glu
         35                  40                  45

Asn Asn Tyr Lys Thr Thr Pro Pro Val Leu Asp Ser Asp Gly Ser Phe
     50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 20
<211> LENGTH: 113

```
<212> TYPE: PRT
<213> ORGANISM: Artificial Sequence
<220> FEATURE:
<223> OTHER INFORMATION: Nivolumab analog heavy chain variable region

<400> SEQUENCE: 20

Gln Val Gln Leu Val Glu Ser Gly Gly Gly Val Val Gln Pro Gly Arg
 1               5                  10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 21
<211> LENGTH: 107
<212> TYPE: PRT
<213> ORGANISM: Artificial Sequence
<220> FEATURE:
<223> OTHER INFORMATION: Nivolumab analog light chain variable region

<400> SEQUENCE: 21

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 22
<211> LENGTH: 5
<212> TYPE: PRT
<213> ORGANISM: Artificial Sequence
<220> FEATURE:
<223> OTHER INFORMATION: HCDR1

<400> SEQUENCE: 22

Phe Tyr Phe Trp Ser
 1               5

<210> SEQ ID NO 23
<211> LENGTH: 16
<212> TYPE: PRT
<213> ORGANISM: Artificial Sequence
```

```
<220> FEATURE:
<223> OTHER INFORMATION: HCDR2

<400> SEQUENCE: 23

Tyr Ile Tyr Tyr Ser Gly Ser Thr Ser Phe Asn Pro Ser Leu Lys Ser
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: HCDR3

<400> SEQUENCE: 24

Gly Gly Tyr Thr Gly Tyr Gly Gly Asp Trp Phe Asp Pro
1               5                   10

<210> SEQ ID NO 25
<211> LENGTH: 5
<212> TYPE: PRT
<213> ORGANISM: Artificial Sequence
<220> FEATURE:
<223> OTHER INFORMATION: HCDR1

<400> SEQUENCE: 25

Phe Asp Phe Trp Ser
1               5

<210> SEQ ID NO 26
<211> LENGTH: 16
<212> TYPE: PRT
<213> ORGANISM: Artificial Sequence
<220> FEATURE:
<223> OTHER INFORMATION: HCDR2

<400> SEQUENCE: 26

Tyr Ile Tyr Tyr Ser Gly Ser Trp Ser Leu Asn Pro Ser Phe Lys Gly
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: HCDR3

<400> SEQUENCE: 27

Gly Gly Tyr Thr Gly Tyr Gly Gly Asp Trp Phe Asp Pro
1               5                   10

<210> SEQ ID NO 28
<211> LENGTH: 5
<212> TYPE: PRT
<213> ORGANISM: Artificial Sequence
<220> FEATURE:
<223> OTHER INFORMATION: HCDR1

<400> SEQUENCE: 28

Phe Glu Phe Trp Ser
1               5

<210> SEQ ID NO 29
<211> LENGTH: 16
<212> TYPE: PRT
<213> ORGANISM: Artificial Sequence
<220> FEATURE:
```

<223> OTHER INFORMATION: HCDR2

<400> SEQUENCE: 29

Tyr Ile Val Tyr Ser Gly Ser His Ser Val Ser Pro Ser Leu Lys Thr
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: HCDR3

<400> SEQUENCE: 30

Gly Gly Tyr Thr Gly His Gly Gly Asp Trp Phe Asp Thr
1               5                   10

<210> SEQ ID NO 31
<211> LENGTH: 5
<212> TYPE: PRT
<213> ORGANISM: Artificial Sequence
<220> FEATURE:
<223> OTHER INFORMATION: HCDR1

<400> SEQUENCE: 31

Arg Phe Ala Leu Ser
1               5

<210> SEQ ID NO 32
<211> LENGTH: 17
<212> TYPE: PRT
<213> ORGANISM: Artificial Sequence
<220> FEATURE:
<223> OTHER INFORMATION: HCDR2

<400> SEQUENCE: 32

Trp Ile Asp Pro Asn Thr Gly Thr Pro Thr Tyr Ala Gln Asp Phe Thr
1               5                   10                  15

Gly

<210> SEQ ID NO 33
<211> LENGTH: 18
<212> TYPE: PRT
<213> ORGANISM: Artificial Sequence
<220> FEATURE:
<223> OTHER INFORMATION: HCDR3

<400> SEQUENCE: 33

Ser Leu Gly Tyr Cys Gly Ser Asp Ile Cys Tyr Pro Asn Gly Ile Leu
1               5                   10                  15

Asp Asn

<210> SEQ ID NO 34
<211> LENGTH: 5
<212> TYPE: PRT
<213> ORGANISM: Artificial Sequence
<220> FEATURE:
<223> OTHER INFORMATION: HCDR1

<400> SEQUENCE: 34

Arg Phe Ala Val Asn
1               5

<210> SEQ ID NO 35
<211> LENGTH: 17

```
<212> TYPE: PRT
<213> ORGANISM: Artificial Sequence
<220> FEATURE:
<223> OTHER INFORMATION: HCDR2

<400> SEQUENCE: 35

Trp Ile Asp Pro Asn Thr Gly Thr Pro Thr Tyr Ala Gln Gly Val Thr
1               5                   10                  15
Asn

<210> SEQ ID NO 36
<211> LENGTH: 18
<212> TYPE: PRT
<213> ORGANISM: Artificial Sequence
<220> FEATURE:
<223> OTHER INFORMATION: HCDR3

<400> SEQUENCE: 36

Ser Leu Gly Tyr Cys Ser Ser Asp Ile Cys Tyr Pro Asn Leu Ile Phe
1               5                   10                  15
Asp Asn

<210> SEQ ID NO 37
<211> LENGTH: 5
<212> TYPE: PRT
<213> ORGANISM: Artificial Sequence
<220> FEATURE:
<223> OTHER INFORMATION: HCDR1

<400> SEQUENCE: 37

Arg Phe Ala Leu His
1               5

<210> SEQ ID NO 38
<211> LENGTH: 17
<212> TYPE: PRT
<213> ORGANISM: Artificial Sequence
<220> FEATURE:
<223> OTHER INFORMATION: HCDR2

<400> SEQUENCE: 38

Trp Ile Asp Pro Asn Thr Gly Thr Pro Thr Phe Ala Gln Gly Val Thr
1               5                   10                  15
Gly

<210> SEQ ID NO 39
<211> LENGTH: 18
<212> TYPE: PRT
<213> ORGANISM: Artificial Sequence
<220> FEATURE:
<223> OTHER INFORMATION: HCDR3

<400> SEQUENCE: 39

Ser Leu Gly Tyr Cys Asp Ser Asp Ile Cys Tyr Pro Asn Trp Ile Phe
1               5                   10                  15
Asp Asn

<210> SEQ ID NO 40
<211> LENGTH: 5
<212> TYPE: PRT
<213> ORGANISM: Artificial Sequence
<220> FEATURE:
<223> OTHER INFORMATION: HCDR

<400> SEQUENCE: 40
```

Tyr His Phe Trp Ser
1               5

<210> SEQ ID NO 41
<211> LENGTH: 16
<212> TYPE: PRT
<213> ORGANISM: Artificial Sequence
<220> FEATURE:
<223> OTHER INFORMATION: HCDR2

<400> SEQUENCE: 41

Tyr Ile Val Tyr Ser Gly Ser Tyr Asn Val Asn Pro Ser Leu Lys Thr
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: HCDR3

<400> SEQUENCE: 42

Gly Gly Tyr Thr Gly Tyr Gly Gly Asp Trp Phe Asp Pro
1               5                   10

<210> SEQ ID NO 43
<211> LENGTH: 5
<212> TYPE: PRT
<213> ORGANISM: Artificial Sequence
<220> FEATURE:
<223> OTHER INFORMATION: HCDR1

<400> SEQUENCE: 43

Tyr His Phe Trp Ser
1               5

<210> SEQ ID NO 44
<211> LENGTH: 16
<212> TYPE: PRT
<213> ORGANISM: Artificial Sequence
<220> FEATURE:
<223> OTHER INFORMATION: HCDR2

<400> SEQUENCE: 44

Tyr Ile Val Tyr Ser Gly Ser Tyr Asn Val Asn Pro Ser Leu Lys Thr
1               5                   10                  15

<210> SEQ ID NO 45
<211> LENGTH: 13
<212> TYPE: PRT
<213> ORGANISM: Artificial Sequence
<220> FEATURE:
<223> OTHER INFORMATION: HCDR3

<400> SEQUENCE: 45

Gly Gly Tyr Thr Gly Tyr Gly Gly Asp Trp Phe Asp Pro
1               5                   10

<210> SEQ ID NO 46
<211> LENGTH: 5
<212> TYPE: PRT
<213> ORGANISM: Artificial Sequence
<220> FEATURE:
<223> OTHER INFORMATION: HCDR1

<400> SEQUENCE: 46

```
Arg Phe Ala Leu His
1               5

<210> SEQ ID NO 47
<211> LENGTH: 17
<212> TYPE: PRT
<213> ORGANISM: Artificial Sequence
<220> FEATURE:
<223> OTHER INFORMATION: HCDR2

<400> SEQUENCE: 47

Trp Ile Asp Pro Asn Thr Gly Thr Pro Thr Phe Ala Gln Gly Val Thr
1               5                   10                  15

Gly

<210> SEQ ID NO 48
<211> LENGTH: 18
<212> TYPE: PRT
<213> ORGANISM: Artificial Sequence
<220> FEATURE:
<223> OTHER INFORMATION: HCDR3

<400> SEQUENCE: 48

Ser Leu Gly Tyr Cys Asp Ser Asp Ile Cys Tyr Pro Asn Trp Ile Phe
1               5                   10                  15

Asp Asn

<210> SEQ ID NO 49
<211> LENGTH: 6
<212> TYPE: PRT
<213> ORGANISM: Artificial Sequence
<220> FEATURE:
<223> OTHER INFORMATION: LCDR1

<400> SEQUENCE: 49

Gln Ser Ile Ser Ser Tyr
1               5

<210> SEQ ID NO 50
<211> LENGTH: 3
<212> TYPE: PRT
<213> ORGANISM: Artificial Sequence
<220> FEATURE:
<223> OTHER INFORMATION: LCDR2

<400> SEQUENCE: 50

Ala Ala Ser
1

<210> SEQ ID NO 51
<211> LENGTH: 9
<212> TYPE: PRT
<213> ORGANISM: Artificial Sequence
<220> FEATURE:
<223> OTHER INFORMATION: LCDR3

<400> SEQUENCE: 51

Gln Gln Ser Tyr Ser Thr Pro Pro Thr
1               5

<210> SEQ ID NO 52
<211> LENGTH: 108
<212> TYPE: PRT
<213> ORGANISM: Artificial Sequence
<220> FEATURE:
<223> OTHER INFORMATION: Light chain variable region
```

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: Light chain variable region

<400> SEQUENCE: 53

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 54
<211> LENGTH: 108
<212> TYPE: PRT
<213> ORGANISM: Artificial Sequence
<220> FEATURE:
<223> OTHER INFORMATION: Light chain variable region

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

```
Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 55
<211> LENGTH: 108
<212> TYPE: PRT
<213> ORGANISM: Artificial Sequence
<220> FEATURE:
<223> OTHER INFORMATION: Light chain variable region

<400> SEQUENCE: 55

Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95

Trp Val Phe Gly Gly Gly Thr Lys Leu Thr Val Leu
            100                 105

<210> SEQ ID NO 56
<211> LENGTH: 95
<212> TYPE: PRT
<213> ORGANISM: Artificial Sequence
<220> FEATURE:
<223> OTHER INFORMATION: V region

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 57
<211> LENGTH: 95
<212> TYPE: PRT
<213> ORGANISM: Artificial Sequence
<220> FEATURE:
<223> OTHER INFORMATION: V region

<400> SEQUENCE: 57

Glu Ile Val Met Thr Gln Ser Pro Ala Thr Leu Ser Val Ser Pro Gly
1               5                   10                  15
```

```
Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95
```

<210> SEQ ID NO 58
<211> LENGTH: 96
<212> TYPE: PRT
<213> ORGANISM: Artificial Sequence
<220> FEATURE:
<223> OTHER INFORMATION: V region

<400> SEQUENCE: 58

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

<210> SEQ ID NO 59
<211> LENGTH: 96
<212> TYPE: PRT
<213> ORGANISM: Artificial Sequence
<220> FEATURE:
<223> OTHER INFORMATION: V region

<400> SEQUENCE: 59

```
Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
                20                  25                  30

Tyr Trp Tyr Gln Gln Lys Ser Gly Gln Ala Pro Val Leu Val Ile Tyr
            35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95
```

<210> SEQ ID NO 60
<211> LENGTH: 107
<212> TYPE: PRT
<213> ORGANISM: Artificial Sequence
<220> FEATURE:
<223> OTHER INFORMATION: Light chain constant region

```
<400> SEQUENCE: 60

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 61
<211> LENGTH: 5
<212> TYPE: PRT
<213> ORGANISM: Artificial Sequence
<220> FEATURE:
<223> OTHER INFORMATION: HCDR1
<220> FEATURE:
<221> NAME/KEY: VARIANT
<222> LOCATION: (1)..(1)
<223> OTHER INFORMATION: can be F, Y, T, or H
<220> FEATURE:
<221> NAME/KEY: VARIANT
<222> LOCATION: (2)..(2)
<223> OTHER INFORMATION: can be Y, Q, E, H, or D
<220> FEATURE:
<221> NAME/KEY: VARIANT
<222> LOCATION: (4)..(4)
<223> OTHER INFORMATION: can be W, or Y

<400> SEQUENCE: 61

Xaa Xaa Phe Xaa Ser
1               5

<210> SEQ ID NO 62
<211> LENGTH: 16
<212> TYPE: PRT
<213> ORGANISM: Artificial Sequence
<220> FEATURE:
<223> OTHER INFORMATION: HCDR2
<220> FEATURE:
<221> NAME/KEY: VARIANT
<222> LOCATION: (3)..(3)
<223> OTHER INFORMATION: can be Y, V, or I
<220> FEATURE:
<221> NAME/KEY: VARIANT
<222> LOCATION: (7)..(7)
<223> OTHER INFORMATION: can be S, or G
<220> FEATURE:
<221> NAME/KEY: VARIANT
<222> LOCATION: (8)..(8)
<223> OTHER INFORMATION: can be T, Y, S, H, N, W, L, or Q
<220> FEATURE:
<221> NAME/KEY: VARIANT
<222> LOCATION: (9)..(9)
<223> OTHER INFORMATION: can be S, or N
<220> FEATURE:
<221> NAME/KEY: VARIANT
<222> LOCATION: (10)..(10)
<223> OTHER INFORMATION: can be F, V, or L
<220> FEATURE:
<221> NAME/KEY: VARIANT
<222> LOCATION: (11)..(11)
<223> OTHER INFORMATION: can be N, or S
```

-continued

```
<220> FEATURE:
<221> NAME/KEY: VARIANT
<222> LOCATION: (13)..(13)
<223> OTHER INFORMATION: can be S or A
<220> FEATURE:
<221> NAME/KEY: VARIANT
<222> LOCATION: (14)..(14)
<223> OTHER INFORMATION: can be F or L
<220> FEATURE:
<221> NAME/KEY: VARIANT
<222> LOCATION: (16)..(16)
<223> OTHER INFORMATION: can be S, T, G, D, R, or N

<400> SEQUENCE: 62

Tyr Ile Xaa Tyr Ser Gly Xaa Xaa Xaa Xaa Pro Xaa Xaa Lys Xaa
1               5                   10                  15

<210> SEQ ID NO 63
<211> LENGTH: 13
<212> TYPE: PRT
<213> ORGANISM: Artificial Sequence
<220> FEATURE:
<223> OTHER INFORMATION: HCDR3
<220> FEATURE:
<221> NAME/KEY: VARIANT
<222> LOCATION: (6)..(6)
<223> OTHER INFORMATION: can be Y, H, V, or A
<220> FEATURE:
<221> NAME/KEY: VARIANT
<222> LOCATION: (13)..(13)
<223> OTHER INFORMATION: can be P, V, Y, W, F, T, Q, H, or S

<400> SEQUENCE: 63

Gly Gly Tyr Thr Gly Xaa Gly Gly Asp Trp Phe Asp Xaa
1               5                   10

<210> SEQ ID NO 64
<211> LENGTH: 5
<212> TYPE: PRT
<213> ORGANISM: Artificial Sequence
<220> FEATURE:
<223> OTHER INFORMATION: HCDR1
<220> FEATURE:
<221> NAME/KEY: VARIANT
<222> LOCATION: (2)..(2)
<223> OTHER INFORMATION: can be F, or Y
<220> FEATURE:
<221> NAME/KEY: VARIANT
<222> LOCATION: (3)..(3)
<223> OTHER INFORMATION: can be T, A, or V
<220> FEATURE:
<221> NAME/KEY: VARIANT
<222> LOCATION: (4)..(4)
<223> OTHER INFORMATION: can be M, L, or V
<220> FEATURE:
<221> NAME/KEY: VARIANT
<222> LOCATION: (5)..(5)
<223> OTHER INFORMATION: can be S, H, N, V, or T

<400> SEQUENCE: 64

Arg Xaa Xaa Xaa Xaa
1               5

<210> SEQ ID NO 65
<211> LENGTH: 17
<212> TYPE: PRT
<213> ORGANISM: Artificial Sequence
<220> FEATURE:
<223> OTHER INFORMATION: HCDR2
<220> FEATURE:
<221> NAME/KEY: VARIANT
<222> LOCATION: (3)..(3)
<223> OTHER INFORMATION: can be N, or D
```

```
<220> FEATURE:
<221> NAME/KEY: VARIANT
<222> LOCATION: (4)..(4)
<223> OTHER INFORMATION: can be P, S, or T
<220> FEATURE:
<221> NAME/KEY: VARIANT
<222> LOCATION: (5)..(5)
<223> OTHER INFORMATION: can be N, or Q
<220> FEATURE:
<221> NAME/KEY: VARIANT
<222> LOCATION: (6)..(6)
<223> OTHER INFORMATION: can be T, or D
<220> FEATURE:
<221> NAME/KEY: VARIANT
<222> LOCATION: (8)..(8)
<223> OTHER INFORMATION: can be N, S, T, K, L, or E
<220> FEATURE:
<221> NAME/KEY: VARIANT
<222> LOCATION: (9)..(9)
<223> OTHER INFORMATION: can be P, Y, A, H, or F
<220> FEATURE:
<221> NAME/KEY: VARIANT
<222> LOCATION: (10)..(10)
<223> OTHER INFORMATION: can be T, or S
<220> FEATURE:
<221> NAME/KEY: VARIANT
<222> LOCATION: (11)..(11)
<223> OTHER INFORMATION: can be Y, F, or H
<220> FEATURE:
<221> NAME/KEY: VARIANT
<222> LOCATION: (12)..(12)
<223> OTHER INFORMATION: can be A, G, V, or F
<220> FEATURE:
<221> NAME/KEY: VARIANT
<222> LOCATION: (13)..(13)
<223> OTHER INFORMATION: can be Q, R, N, L, T, or S
<220> FEATURE:
<221> NAME/KEY: VARIANT
<222> LOCATION: (14)..(14)
<223> OTHER INFORMATION: can be D, A, G, or S
<220> FEATURE:
<221> NAME/KEY: VARIANT
<222> LOCATION: (15)..(15)
<223> OTHER INFORMATION: can be F, V, or A
<220> FEATURE:
<221> NAME/KEY: VARIANT
<222> LOCATION: (16)..(16)
<223> OTHER INFORMATION: can be T, K, H, G
<220> FEATURE:
<221> NAME/KEY: VARIANT
<222> LOCATION: (17)..(17)
<223> OTHER INFORMATION: can be G, N, E, or D

<400> SEQUENCE: 65

Trp Ile Xaa Xaa Xaa Xaa Gly Xaa Xaa Xaa Xaa Xaa Xaa Xaa Xaa Xaa
1               5                   10                  15

Xaa

<210> SEQ ID NO 66
<211> LENGTH: 18
<212> TYPE: PRT
<213> ORGANISM: Artificial Sequence
<220> FEATURE:
<223> OTHER INFORMATION: HCDR3
<220> FEATURE:
<221> NAME/KEY: VARIANT
<222> LOCATION: (1)..(1)
<223> OTHER INFORMATION: can be I, S, or V
<220> FEATURE:
<221> NAME/KEY: VARIANT
<222> LOCATION: (2)..(2)
<223> OTHER INFORMATION: can be L, Q, or N
<220> FEATURE:
<221> NAME/KEY: VARIANT
<222> LOCATION: (6)..(6)
<223> OTHER INFORMATION: can be N, G, S, or D
```

```
<220> FEATURE:
<221> NAME/KEY: VARIANT
<222> LOCATION: (7)..(7)
<223> OTHER INFORMATION: can be T, S, P, N, or E
<220> FEATURE:
<221> NAME/KEY: VARIANT
<222> LOCATION: (9)..(9)
<223> OTHER INFORMATION: can be N, or I
<220> FEATURE:
<221> NAME/KEY: VARIANT
<222> LOCATION: (14)..(14)
<223> OTHER INFORMATION: can be W, G, Q, H, W, A, or L
<220> FEATURE:
<221> NAME/KEY: VARIANT
<222> LOCATION: (15)..(15)
<223> OTHER INFORMATION: can be I, V, or L
<220> FEATURE:
<221> NAME/KEY: VARIANT
<222> LOCATION: (16)..(16)
<223> OTHER INFORMATION: can be F, L, or I
<220> FEATURE:
<221> NAME/KEY: VARIANT
<222> LOCATION: (18)..(18)
<223> OTHER INFORMATION: can be Y, S, N, I, R, H, V, T, K, A, or L

<400> SEQUENCE: 66

Xaa Xaa Gly Tyr Cys Xaa Xaa Asp Xaa Cys Tyr Pro Asn Xaa Xaa Xaa
1               5                   10                  15

Asp Xaa
```